United States Patent
Hacohen et al.

(10) Patent No.: US 11,634,777 B2
(45) Date of Patent: Apr. 25, 2023

(54) RESISTANCE TO CHECKPOINT BLOCKADE THERAPY

(71) Applicant: THE GENERAL HOSPITAL CORPORATION, Boston, MA (US)

(72) Inventors: Nir Hacohen, Boston, MA (US); Moshe Sade-Feldman, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 438 days.

(21) Appl. No.: 16/477,827

(22) PCT Filed: Jan. 12, 2018

(86) PCT No.: PCT/US2018/013637
§ 371 (c)(1),
(2) Date: Jul. 12, 2019

(87) PCT Pub. No.: WO2018/132749
PCT Pub. Date: Jul. 19, 2018

(65) Prior Publication Data
US 2019/0367992 A1 Dec. 5, 2019

Related U.S. Application Data

(60) Provisional application No. 62/446,138, filed on Jan. 13, 2017.

(51) Int. Cl.
*C12Q 1/6886* (2018.01)
*C07K 16/28* (2006.01)
*A61K 45/06* (2006.01)

(52) U.S. Cl.
CPC ........ *C12Q 1/6886* (2013.01); *C07K 16/2818* (2013.01); *C07K 16/2827* (2013.01); *C07K 16/2878* (2013.01); *A61K 45/06* (2013.01); *C12Q 2600/106* (2013.01); *C12Q 2600/156* (2013.01)

(58) Field of Classification Search
CPC .................................................. C12Q 1/6886
USPC ..................................................... 424/133.1
See application file for complete search history.

(56) References Cited

U.S. PATENT DOCUMENTS

2013/0149695 A1 6/2013 Lee
2018/0051347 A1 2/2018 Ribas

FOREIGN PATENT DOCUMENTS

WO 2016100975 A1 6/2016
WO 2018132749 A1 7/2018

OTHER PUBLICATIONS

McEvoy et al. (Tissue Antigens, 2002, 60: 235-243).*
Campo et al (Scandinavian Journal of Immunology, 2009, 70: 125-135).*
Thompson et al (J Immunother Cancer, 2020, 8, e000974, 1-9).*
Reichel et al (Blood, 2015, 125(7): 1061-1072).*
Dubois et al (Clin Cancer Res, 2016, 22(12): 2919-2928).*
Wang et al (J Clin Invest, 1993, 91(2): 684-692).*
Molina-Vila et al (Ann Transl Med, 2015, 3(20):309, 6 pages).*
Morrissey et al (Clin Trans Sci, 2016, 9: 89-104).*
Amaral, et al., "Acquired resistance mechanisms to immunotherapy", Annals of translational medicine. Dec. 2016, 4 pages.
Chen, et al., "Analysis of Immune Signatures in Longitudinal Tumor Samples Yields Insight into Biomarkers of Response and Mechanisms of Resistance to Immune Checkpoint Blockade", Cancer Discovery. Aug. 2016, Epub Jun. 14, 2016, vol. 6, No. 8; pp. 827-837; abstract, p. 828, 2nd col. 2nd paragraph, p. 830, 1st col. 3rd paragraph p. 834, 1st col. 3rd paragraph.
Garrido, et al., "The urgent need to recover MHC class I in cancers for effective immunotherapy", Current Opinion in Immunology. Apr. 2016, 8 pages.
O'Donnell, et al., "Acquired resistance to anti-PD1 therapy: checkmate to checkpoint blockade?", Genome Medicine. Oct. 25, 2016, vol. 8, 3 pages.
Rooney, et al., "Molecular and genetic properties of tumors associated with local immune cytolytic activity", Cell. Jan. 15, 2015, vol. 160, 27 pages.
Sade-Feldman, et al., "Resistance to checkpoint blockade therapy through inactivation of antigen presentation", Nature Communication. Oct. 26, 2017, vol. 8. No. 1, 11 pages.
Thomas, "International Search Report and Written Opinion of PCT/US2018/013637", dated Mar. 28, 2018.
Igney, et al., "Immune escape of tumors: apoptosis resistance and tumor counterattack", J. Leukoc. Biol. 71: 907-920; 2002.
Restifo, et al., "Loss of functional beta 2-microglobulin in metastatic melanomas from five patients receiving Immunotherapy", J Natl Cancer Inst. Jan. 17, 1996; 88(2): 100-108, 19 pages.
Wittmann-Regis, "International Preliminary Report on Patentability of PCT/US2018/013637", dated Jul. 25, 2019, 10 pages.

* cited by examiner

*Primary Examiner* — Sean E Aeder
(74) *Attorney, Agent, or Firm* — F. Brent Nix; Johnson, Marcou, Isaacs & Nix, LLC

(57) ABSTRACT

Provided herein are methods of determining resistance to checkpoint blockade (CPB) therapy in a cancer patient, methods of typing tumor cells of a cancer patient, methods of assigning treatment to a cancer patient and methods of treatment of a cancer patient based on determining in a tumor sample of said patient, reduced expression of a gene relating to antigen processing pathway or a product thereof, or a modification causing said reduced expression, wherein the presence of said reduced expression or modification is indicative of resistance to CPB therapy.

12 Claims, 15 Drawing Sheets
Specification includes a Sequence Listing.

SEQUENCE LISTING

<160> NUMBER OF SEQ ID NOS: 3

<210> SEQ ID NO 1
<211> LENGTH: 12
<212> TYPE: DNA
<213> ORGANISM: Artificial Sequence
<220> FEATURE:
<223> OTHER INFORMATION: Synthetic

<400> SEQUENCE: 1
ctctctcttt ct                                                           12

<210> SEQ ID NO 2
<211> LENGTH: 19
<212> TYPE: DNA
<213> ORGANISM: Artificial Sequence
<220> FEATURE:
<223> OTHER INFORMATION: Synthetic Primer B2M_F

<400> SEQUENCE: 2
ggcattcctg aagctgaca                                                    19

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer B2M_R

<400> SEQUENCE: 3
gaagtcacgg agcgagagag                                                   20

RESISTANCE TO CHECKPOINT BLOCKADE THERAPY

CROSS-REFERENCE TO RELATED APPLICATIONS

This application is a 35 U.S.C. § 371 national stage of International Application No. PCT/US2018/013637 filed on Jan. 12, 2018, which claims the benefit of U.S. Provisional Application No. 62/446,138, filed Jan. 13, 2017. The entire contents of the above-identified applications are hereby fully incorporated herein by reference.

REFERENCE TO AN ELECTRONIC SEQUENCE LISTING

The contents of the electronic sequence listing (BROD_0810_ST25.txt"; Size is 913 bytes and it was created on Jun. 3, 2019) is herein incorporated by reference in its entirety.

FIELD OF THE INVENTION

The present application relates to methods for determining resistance to checkpoint blockade (CPB) therapy in cancer patients, and method for treatment of cancer patients that are resistant to CPB therapy.

BACKGROUND OF THE INVENTION

Although immune checkpoint blockade (CPB) with anti-cytotoxic T-lymphocyte associated protein 4 (CTLA4), anti-programmed death 1 (PD1) or anti-PD ligand 1 (PD-L1) antibodies is associated with significant and prolonged responses in 15-40% of patients with metastatic melanoma, treatment refractory disease and progression after initial response remain major causes of mortality[1-5]. While attention has been given to identifying predictors of response[6-8], the mechanisms of clinically acquired resistance to CPB have not been reported. Knowing the mechanisms of resistance to CPB therapies would enable us to optimally select patients for therapy, identify new therapeutic targets, and increase the chance of durable responses. CPB targets inhibitory immune checkpoints expressed on cancer-cells (PD-L1) or tumor infiltrating T cells (TILs) (PD1, CTLA4), unleashing pre-existing anti-cancer immunity[9]. The efficacy of CPB depends on cytotoxic CD8+ T cell (CTL) recognition of cancer-specific antigens presented on human leukocyte antigen (HLA) class-I complexes.

Comprehensive knowledge of the mechanisms underlying response and resistance to CPB, coupled with the ability to reliably and cost-effectively diagnose these mechanisms in the clinic, should inform therapeutic strategies that induce long-term responses in more patients. Indeed, recent studies suggested several clinical predictors of CPB response: PDL-1 expression, transcriptional signatures related to tumor cell mesenchymal transition, microbiota, increased frequencies of suppressive immune cells (myeloid derived suppressor cells, MDSCs), effector T cell landscape, and high mutational and neoantigen loads[6,7,20]. While these parameters are associated with response, not all patients with positive predictors respond to therapy.

Thus, there is a need for improved methods to identify mechanisms of resistance to CPB therapy in cancer patients and use this information to more effectively guide treatment regimens for patients.

Citation or identification of any document in this application is not an admission that such document is available as prior art to the present invention.

SUMMARY OF THE INVENTION

In certain example embodiments, a method of detecting cancer in patients that are resistant to checkpoint blockade (CPB) therapy comprise detecting, in a biological sample from a patient suffering from a cancer, one or more genetic modifications in a gene related to antigen processing and/or presentation. In certain example embodiments, a method of predicting overall survival in cancer patients, comprising detecting, in a biological sample from a patient suffering from a cancer, one or more genetic modifications in a gene related to antigen processing, wherein detecting one or more genetic modifications in a gene related to antigen processing indicates lower overall survival. In certain example embodiments, the genetic modification results from a mutation or deletion in chromosome 15. In certain example embodiments, the one or more genetic modifications results in loss of heterozygosity (LOH) of the beta-2-microglobulin (B2M) gene. In certain example embodiments, the one or more genetic modifications result in reduced expression of the beta-2-microglobulin (B2M) gene. The genetic modification resulting in reduced expression of B2M may comprise a frame-shift mutation in exon 1 or exon 2 of B2M. In certain example embodiments, the frame-shift mutation may comprise p.Leu13fs, p.Ser14fs, p.Gly63fs, or a combination thereof.

The genetic modification by direct detection of the genetic modification, for example by sequencing and/or amplification of the genetic modification, or by detection using a labeled oligonucleotide probe. Alternatively, the genetic modification may be detected by reduced expression of a gene product. For example, by detection of a mRNA or protein product of the expressed gene. In certain example embodiments, the sample may be a tumor biopsy sample. In certain other example embodiments, the sample may be a blood sample and comprises detection of the genetic modification in cell free DNA (cfDNA).

In particular embodiments, the gene related to antigen processing pathway is a human leukocyte antigen (HLA) gene. Preferably, said HLA gene is HLA-C. In one embodiment, the modification in said HLA gene, preferably HLA-C, is mutation p.W23C.

In particular embodiments, said detecting cancers cells resistant to CPB therapy is carried out in a biological sample of a patient that has not received CPB therapy and/or is carried out in a biological sample of a patient prior to CPB therapy. In other example embodiments, said detecting cancers cells resistant to CPB therapy is carried out in a biological sample of a patient receiving CPB therapy. In yet another embodiment, said detecting cancers cells resistant to CPB therapy is carried out in a biological sample of a patient both prior to and while receiving CPB therapy.

In particular embodiments, the methods for detecting cancers cells resistant to CPB therapy further comprises treating said patient with a therapy other than CPB therapy if the genetic modification is detected.

In particular embodiments, said treatment other than CPB treatment is selected from the group consisting of NK cell therapy, radiotherapy, chemotherapy and tumor-specific monoclonal antibodies. Said NK cell therapy may be adoptive NK cell therapy and/or treatment with an agonistic antibody directed against an NK cell receptor. Said antibody may be an antibody selected from anti-CD137, anti-CD27, and anti-OX40.

In a further aspect, the invention provides methods for treating cancer patients showing resistance to CPB therapy, said method comprising detecting a genetic modification in an antigen processing pathway gene, and treating the patient with a CPB therapy if the genetic modification is not detected, or treating the patient with a therapy other than CPB therapy.

In particular embodiments, said methods further comprise restoring loss of function caused by the one or more genetic modifications using gene therapy.

In certain other example embodiments, kits for detecting cancer cells resistant to CPB therapy comprise reagents for detecting the above described one or more genetic modifications.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

DETAILED DESCRIPTION OF THE INVENTION

Figure 1:
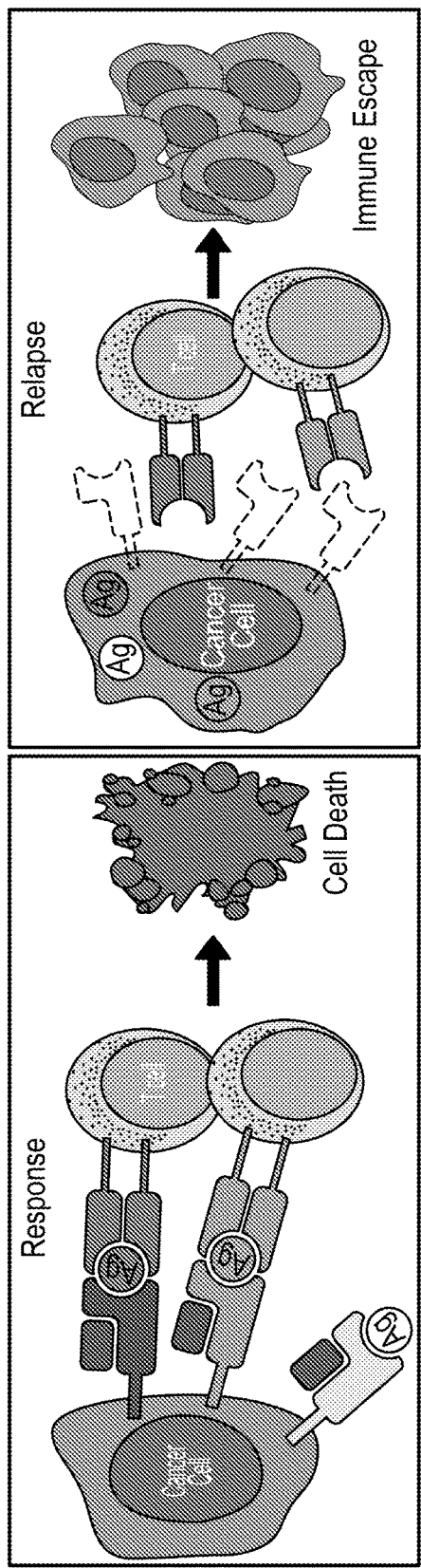
FIG. 1 is a schematic showing a way in which resistance to CPB may be acquired due to loss of B2M.
Figure 1:
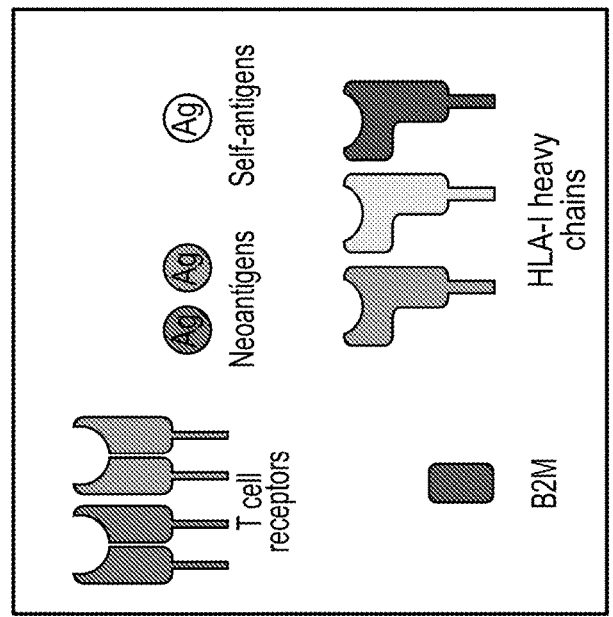

Before the present methods of the invention are described, it is to be understood that this invention is not limited to particular methods, components, products or combinations described, as such methods, components, products and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of", as well as the terms "consisting essentially of", "consists essentially" and "consists essentially of". It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. It may be advantageous in the practice of the invention to be in compliance with Art. 53(c) EPC and Rule 28(b) and (c) EPC. Nothing herein is intended as a promise.

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−20% or less, preferably +/−10% or less, more preferably +/−5% or less, and still more preferably +/−1% or less of and from the specified value, insofar such variations are appropriate to perform in the disclosed invention. It is to be understood that the value to which the modifier "about" or "approximately" refers is itself also specifically, and preferably, disclosed.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The term "pharmaceutically acceptable" refers to approved or approvable by a regulatory agency of the Federal or a state government or listed in the U.S. Pharmacopeia or other generally recognized pharmacopeia for use in animals, including humans.

A "pharmaceutically acceptable excipient, carrier or diluent" refers to an excipient, carrier or diluent that can be administered to a subject, together with an agent, and which does not destroy the pharmacological activity thereof and is nontoxic when administered in doses sufficient to deliver a therapeutic amount of the agent.

A "pharmaceutically acceptable salt" as referred to herein may be an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—(CH2)n-COOH where n is 0-4, and the like. Similarly, pharmaceutically acceptable cations include, but are not limited to sodium, potassium, calcium, aluminum, lithium and ammonium. Those of ordinary skill in the art will recognize from this disclosure and the knowledge in the art that further pharmaceutically acceptable salts for the pooled tumor specific neoantigens provided herein, including those listed by Remington's Pharmaceutical Sciences, 17th ed., Mack Publishing Company, Easton, Pa., p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in an appropriate solvent.

The terms "individual" or "patient" as used herein refers to an animal which is the object of treatment, observation, or experiment. By way of example only, a subject includes, but is not limited to, a mammal, including, but not limited to, a human or a non-human mammal, such as a non-human primate, bovine, equine, canine, ovine, or feline.

The terms "treat," "treated," "treating," "treatment," and the like are meant to refer to reducing or ameliorating a disorder and/or symptoms associated therewith (e.g., a neoplasia or tumor). "Treating" may refer to administration of the combination therapy to a subject after the onset, or suspected onset, of a cancer. "Treating" includes the concepts of "alleviating", which refers to lessening the frequency of occurrence or recurrence, or the severity, of any symptoms or other ill effects related to a cancer and/or the side effects associated with cancer therapy. The term "treating" also encompasses the concept of "managing" which refers to reducing the severity of a particular disease or disorder in a patient or delaying its recurrence, e.g., lengthening the period of remission in a patient who had suffered from the disease. It is appreciated that, although not precluded, treating a disorder or condition does not require that the disorder, condition, or symptoms associated therewith be completely eliminated.

As used herein, the terms "prevent," "preventing," "prevention," "prophylactic treatment," and the like, refer to reducing the probability of developing a disease or condition in a subject, who does not have, but is at risk of or susceptible to developing a disease or condition.

The term "prime/boost" or "prime/boost dosing regimen" is meant to refer to the successive administrations of a vaccine or immunogenic or immunological compositions. The priming administration (priming) is the administration of a first vaccine or immunogenic or immunological composition type and may comprise one, two or more administrations. The boost administration is the second administration of a vaccine or immunogenic or immunological composition type and may comprise one, two or more administrations, and, for instance, may comprise or consist essentially of annual administrations. In certain embodiments, administration of the neoplasia vaccine or immunogenic composition is in a prime/boost dosing regimen.

The term "therapeutic effect" refers to some extent of relief of one or more of the symptoms of a disorder (e.g., a neoplasia or tumor) or its associated pathology. "Therapeutically effective amount" as used herein refers to an amount of an agent which is effective, upon single or multiple dose administration to the cell or subject, in prolonging the survivability of the patient with such a disorder, reducing one or more signs or symptoms of the disorder, preventing or delaying, and the like beyond that expected in the absence of such treatment. "Therapeutically effective amount" is intended to qualify the amount required to achieve a therapeutic effect. A physician or veterinarian having ordinary skill in the art can readily determine and prescribe the "therapeutically effective amount" (e.g., ED50) of the pharmaceutical composition required. For example, the physician or veterinarian could start doses of the compounds of the invention employed in a pharmaceutical composition at levels lower than that required in order to achieve the desired therapeutic effect and gradually increase the dosage until the desired effect is achieved.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Immune checkpoints are inhibitory pathways that slow down or stop immune reactions and prevent excessive tissue damage from uncontrolled activity of immune cells. "Checkpoint blockade (CPB) therapy" refers to therapy that inhibits the inhibitory pathways, allowing more extensive immune activity. Such therapy can comprise treatment with any small molecule chemical compound, antibody, nucleic acid molecule, or polypeptide, or fragment thereof, that inhibits the inhibitory pathways. "Checkpoint blockade therapy" may also refer to stimulation of a preexisting immune response. In certain embodiments, CPB therapy is therapy with an inhibitor of the programmed death-1 (PD-1) pathway, for example an anti-PD1 antibody, such as, but not limited to Nivolumab. In other embodiments, CPB therapy is therapy with an anti-cytotoxic T-lymphocyte-associated antigen-4 (CTLA-4) antibody. In additional embodiments, the CPB therapy is targeted at another member of the CD28/CTLA4 Ig superfamily such as BTLA, LAG3, ICOS, PD-L1 or KIR (Page et al., Annual Review of Medicine 65:27 (2014)). In further additional embodiments, the CPB therapy is targeted at a member of the TNFR superfamily such as CD40, OX40, CD137, GITR, CD27 or TIM-3. In some cases, targeting a checkpoint inhibitor is accomplished with an inhibitory antibody or similar molecule. In other cases, it is accomplished with an agonist for the target; examples of this class include the stimulatory targets OX40 and GITR. Particularly preferred is CPB therapy comprising therapy with antibodies selected from anti-CTLA4, anti-PD1, anti-PD-L1 antibodies and a combination thereof.

A "cancer patient" as used herein refers to an individual that has been diagnosed as having cancer. Examples of cancers include, but are not limited to, a solid tumor such as breast, ovarian, prostate, lung, kidney, gastric, colon, testicular, head and neck, pancreas, brain, melanoma, and other tumors of tissue organs and hematological tumors, such as lymphomas and leukemias, including acute myelogenous leukemia, chronic myelogenous leukemia, chronic lymphocytic leukemia, T cell lymphocytic leukemia, and B cell lymphomas, tumors of the brain and central nervous system (e.g., tumors of the meninges, brain, spinal cord, cranial nerves and other parts of the CNS, such as glioblastomas or medulla blastomas); head and/or neck cancer, breast tumors, tumors of the circulatory system (e.g., heart, mediastinum and pleura, and other intrathoracic organs, vascular tumors, and tumor-associated vascular tissue); tumors of the blood and lymphatic system (e.g., Hodgkin's disease, Non-Hodgkin's disease lymphoma, Burkitt's lymphoma, AIDS-related lymphomas, malignant immunoproliferative diseases, multiple myeloma, and malignant plasma cell neoplasms, lymphoid leukemia, myeloid leukemia, acute or chronic lymphocytic leukemia, monocytic leukemia, other leukemias of specific cell type, leukemia of unspecified cell type, unspecified malignant neoplasms of lymphoid, hematopoietic and related tissues, such as diffuse large cell lymphoma, T cell lymphoma or cutaneous T cell lymphoma); tumors of the excretory system (e.g., kidney, renal pelvis, ureter, bladder, and other urinary organs); tumors of the gastrointestinal tract (e.g., esophagus, stomach, small intestine, colon, colorectal, rectosigmoid junction, rectum, anus, and anal canal); tumors involving the liver and intrahepatic bile ducts, gall bladder, and other parts of the biliary tract, pancreas, and other digestive organs; tumors of the oral cavity (e.g., lip, tongue, gum, floor of mouth, palate, parotid gland, salivary glands, tonsil, oropharynx, nasopharynx, pyriform sinus, hypopharynx, and other sites of the oral cavity); tumors of the reproductive system (e.g., vulva, vagina, Cervix uteri, uterus, ovary, and other sites associated with female genital organs, placenta, penis, prostate, testis, and other sites associated with male genital organs); tumors of the respiratory tract (e.g., nasal cavity, middle ear, accessory sinuses, larynx, trachea, bronchus and lung, such as small cell lung cancer and non-small cell lung cancer); tumors of the skeletal system (e.g., bone and articular cartilage of limbs, bone articular cartilage and other sites); tumors of the skin (e.g., malignant melanoma of the skin, non-melanoma skin cancer, basal cell carcinoma of skin, squamous cell carcinoma of skin, mesothelioma, Kaposi's sarcoma); and tumors involving other tissues including peripheral nerves and autonomic nervous system, connective and soft tissue, retroperitoneum and peritoneum, eye, thyroid, adrenal gland, and other endocrine glands and related structures, secondary and unspecified malignant neoplasms of lymph nodes, secondary malignant neoplasm of respiratory and digestive systems and secondary malignant neoplasm of other sites. In a preferred embodiment, said cancer is melanoma, lung cancer, such as non-small-cell lung cancer, prostate cancer, renal-cell cancer or colorectal cancer, most preferably melanoma.

A used herein a "tumor sample" refers to any sample containing tumor cells derived from a cancer patient. Said sample preferably comprises nucleic acids and/or proteins, polypeptide and/or peptides. Preferably, the sample consists essentially of tumor cells. In some embodiments the methods of the invention comprise obtaining such sample from said patient. In another embodiment, said sample has been obtained at an earlier time point and has been stored prior to performing a method of the invention.

As used herein an "antigen processing pathway gene," or "gene relating to antigen processing pathway" refers to a gene involved in any part of antigen presentation, recognition and processing. In particular embodiments, the gene encodes a protein involved in antigen presentation, such part of an MHC class I or class II complexes. MHC class I complexes are heterodimers that consist of two polypeptide chains, α and β-microglobulin (b2m, also referred to herein as B2M). The two chains are linked noncovalently via interaction of b2m and the α3 domain. The a chain is polymorphic and encoded by a HLA gene, the b2m subunit is encoded by the beta-2-microglobulin gene. In one embodiment, said gene encodes a B2M protein.

A "gene product" refers to any product of such gene including proteins, polypeptides, peptides and RNA molecules (i.e. polynucleotides, such as tRNA, rRNA, mRNA). Hence in one embodiment, expression of mRNA, tRNA, rRNA, protein, polypeptide or peptide encoded by said gene relating to antigen processing pathway is determined. In one embodiment, an expression level of said gene product is determined.

As used herein "reduced expression" refers to a reduced or decreased expression of a gene relating to antigen processing pathway or a gene product thereof in the tumor sample as compared to the expression of said gene or gene product in a control. In one embodiment, said control is a sample from a healthy individual, such as a sample of the same tissue as present in the tumor sample of the cancer patient. For instance, if said tumor sample is a sample of a lung tumor and comprises lung tissue, said control is lung tissue of a healthy individual. In one further embodiment, said control is a sample from said cancer patient not comprising a tumor or tumor cells, preferably a sample of the same tissue as present in the tumor sample of the cancer patient. The term "reduced expression" preferably refers to at least a 25% reduction, e.g., at least a 30%, 40%, 50%, 60%, 70%, 75%, 80%, 85%, 90%, 95%, 98% or 99% reduction, relative to such control.

The term "modification causing said reduced expression" refers to a modification in a gene which affects the antigen processing pathway. In particular embodiments, the modification is in the gene relating to antigen processing pathway. Said modification is preferably a modification in a gene selected from B2M, a HLA gene, TAP1 or TAP2. Said modification can be any nucleic acid modification including, but not limited to, a mutation, a deletion, an insertion, a replacement, a ligation, a digestion, a break and a frameshift. Said modification is preferably selected from the group consisting of a mutation, a deletion and a frameshift. In particular embodiments, the modification is a mutation which results in reduced expression of the functional gene product.

In one aspect, the invention provides methods of determining resistance to checkpoint blockade (CPB) therapy or checkpoint inhibitors. The nature of the CPB therapy is not critical to the present invention and examples of suitable agents are described herein. In particular embodiments, the CPB therapy is therapy with antibodies selected from anti-CTLA4, anti-PD1, anti-PD-L1 antibodies and a combination thereof. An exemplary anti-CTLA4 antibody is ipilimumab. An exemplary anti-PD1 antibody is nivolumab. A significant number of cancer patients undergoing CPB therapy, after a first period of regression, become resistant to CPB therapy resulting in progression of the tumor. It is of interest to be able to determine when resistance to CPB is occurring such that treatment can be adapted. It has been found that resistance to CPB therapy is linked to reduced expression of a gene relating to antigen processing pathway or a product thereof. In particular embodiments, the gene is B2M.

The methods as provided herein comprise, detecting, in a biological sample of a patient, one or more genetic modifications to an antigen processing pathway gene. Methods for determining expression of a gene or a product thereof are known in the art and include, but are not limited to, methods of RNA detection, such as but not limited to Northern blotting, RT-qPCR, RNA sequencing and methods of protein detection, such as but not limited to Western blotting, ELISA, RIA, Histochemical detection etc. In particular embodiments, detection of expression is performed by immunohistochemistry. Antibodies suitable for immunological (e.g. immunohistochemical) detection of proteins involved in antigen processing pathway, such as BM2 or HLA proteins, are typically commercially available or can be obtained by routine methods. Where the methods involve determining reduced expression, typically the expression of a gene involved in antigen processing pathway is quantified. In particular embodiments, the expression is quantified relative to a control sample for which expression is set at 100%. In particular embodiments, the reduction of expression is at least 20%, more particularly at least 50%, such as at least 90%. In further embodiments, the expression level is reduced to less than 80%, such as between 50-80%, or to less than 50%, such as between 0-50%, such as between 10-50%. In these embodiments, reduced expression determined in a tumor sample of a patient is indicative of resistance to CPB therapy in said patient.

Additionally or alternatively, the methods involve determining the presence of modifications in the sample, which modifications result in altered expression of the gene or gene product involved in antigen presentation. Modifications in genes can be determined directly by methods such as but not limited to PCR, sequencing, gradient gel electrophoresis etc.

In particular embodiments, the methods involve determining a modification in a gene causing reduced expression of a gene involved in antigen processing pathway or a product thereof. In particular embodiments, the modification is detected in a gene encoding a protein involved in antigen processing, such as those described herein. In particular embodiments, the methods involve determining a modification in the B2M gene. In particular embodiments, the modification is selected from a mutation or a deletion. In particular embodiments, the modification is in exon 1 or exon 2. Multiple mutations resulting in reduced expression of the functional protein have been disclosed for the B2M gene, such as in Madhavi Challa-Malladi et al. 2011; (Cancer Cell 20(6): 728-740). Exemplary missense mutations include, but are not limited to, T62A, T62G, T62C, T80C, G82A, T193G, A245C, C271A, T304G, A353G, T352A; exemplary nonsense mutations include G299A, G309T, C318G, exemplary frameshift mutations include p.Leu13fs, p.Ser14fs and p.Gly63fs. Further examples include 4(54-63), 4(91-101), 4(103-104), 4(97-98), 4(239-240); insT (239-240), InsA(345-346); exemplary splice site mutations include T(+2)A, G(+1)A. However, the detection of modifications need not be limited to those exemplified herein. In particular embodiments, the modification is a chromosomal deletion in a chromosome carrying a gene involved in antigen processing pathway. The BM2 gene is located on chromosome 6, such that a deletion in chromosome 6 can affect BM2 expression.

In particular embodiments, the gene relating to antigen processing pathway is a human leukocyte antigen (HLA) gene, such as HLA-A, HLA-B or HLA-C. An exemplary mutation of the HLA-C gene is p.W23C. However, the detection of modifications need not be limited to those exemplified herein.

Where the methods involve detecting the presence or absence of a modification resulting in decreased expression of a gene involved in antigen processing pathway, the presence of such a modification is indicative of resistance to CPB therapy.

The methods for detecting resistance to CPB therapy of a patient are of particular interest for determining, in a patient receiving CPB therapy, the efficacy of said CPB therapy. Accordingly, in particular embodiments, the methods are performed on a sample of a patient that has received CPB therapy. In these embodiments, the methods can be used to determine the efficacy of CPB therapy in said patient. In particular embodiments, the methods allow prediction of progression of the tumor in said patient. In particular embodiments, the methods are carried out on a patient receiving CPB therapy upon signs of progression of the disease in said patient, such as after signs of clinical progression. In particular embodiments, the methods are carried out on a tumor sample of a patient that has not yet received CPB therapy, such as, but not limited to a patient prior to administering CPB therapy. In these embodiments, the methods are used to predict the efficacy of CPB therapy in said patient.

In particular embodiments, the methods for detecting resistance to CPB therapy further comprises a treatment step. More particularly, the methods provided herein are used to determine the patient's suitability for therapy. In particular embodiments, those patients for which resistance to CPB therapy is determined are selected for treatment with a treatment which is different from CPB therapy. Such therapy may comprise, but is not limited to, one or more of NK cell therapy, radiotherapy, chemotherapy and tumor-specific monoclonal antibodies. Thus, also provided herein are methods of assigning treatment to a cancer patient, said methods comprising determining resistance to CPB therapy using a method as described herein and assigning treatment based on whether or not resistance to CPB therapy is determined in said patient. In particular embodiments, where the patient is determined to be resistant to CPB therapy, the method encompasses assigning a treatment other than said CPB therapy to said patient.

In particular embodiments, the methods for detecting resistance to CPB are envisaged to be carried out on a tumor sample, or a sample comprising or essentially consisting of tumor cells. Accordingly, in particular embodiments, the methods are carried out in vitro. In alternative embodiments, however, the methods for determining decreased expression of a gene involved in antigen presentation or a modification causing said decrease in expression are carried out in vivo.

Also provided are methods to identify suitable therapeutic agents and/or regimes for a given patient. This is of particular interest in the context of treatments which are suspected to elicit resistance to CPB therapy. These methods involve, administering said therapeutic agent or therapeutic regime to said patient and monitoring, using the methods provided herein, whether or not resistance to CPB therapy is obtained in said patient. In particular embodiments, the methods comprise altering said therapeutic agent or regime, upon determination of resistance to CPB therapy in said patient. Similarly, such methods can be used to identify novel therapeutic agents and/or regimes.

Also provided herein are methods of typing tumor cells of a cancer patient based on the presence or absence in said tumor cells of reduced expression of a gene relating to antigen processing or a product thereof, or a modification causing said reduced expression. The methods comprise determining said reduced expression or modification in the cells and typing the cells based thereon. In particular embodiments, the methods are used to determine whether or not the tumor cell is resistant to CPB therapy. These methods are of interest in the screening of agents/regimens that can be used to combat tumor cells which are resistant to CPB therapy and/or agents which are capable of reversing said resistance.

Exemplary alternative treatments for patients that are resistant to CPB therapy include, but are not limited to, NK cell therapy, radiotherapy, chemotherapy and tumor-specific monoclonal antibodies. In particular embodiments, the NK cell therapy is adoptive NK cell therapy and/or treatment with an agonistic antibody directed against an NK cell receptor, such as an antibody is selected from anti-CD137, anti-CD27 and anti-OX40. In particular embodiments, methods of treatment of a cancer patient are provided which methods encompass determining in a tumor sample of the patient whether the tumor is resistant to CPB therapy, and upon determining that the tumor is resistant to CPB therapy, selecting one or more alternative treatments as described herein above for administration to the patient. In particular embodiments, the methods encompass administering the one or more alternative treatments to the patient. In particular embodiments, the methods may encompass continuing the CPB therapy. In alternative embodiments, CPB therapy is stopped and replaced by one or more of the alternative treatments as described herein.

In particular embodiments, methods are provided which encompass addressing the tumor resistance observed for the tumor. Accordingly, in particular embodiments, methods for treating a cancer patient showing resistance to CPB therapy are provided, which methods comprise determining reduced expression of a gene relating to antigen processing pathway or a modification causing said reduced expression in a tumor sample of the patient and restoring expression of said gene relating to antigen processing pathway in the patient. In particular embodiments, expression of the gene is restored by addressing the modification causing the reduced expression. For instance, where reduced expression of a gene involved in antigen machinery is caused by a mutation, this genetic modification can be restored, such as by gene therapy or gene editing. Suitable methods for restoring expression of a gene or gene product are known in the art.

Kits

Reagents, tools, and/or instructions for performing the methods described herein can be provided in a kit. For example, the kit can contain reagents, tools, and instructions for detecting tumor cells in patient samples that are resistant to checkpoint blockade therapy. Such a kit can include reagents for collecting a tissue sample from a patient, such as by biopsy, and reagents for processing the tissue. The kit can also include one or more reagents for performing a gene or gene product expression analysis, such as reagents for performing nucleic acid amplification (e.g RT-PCR, qPCR), sequencing (e.g. next generation sequencing, whole exome sequencing), northern blot, proteomic analysis, or immunohistochemistry to determine expression levels of gene or gene product markers in a sample of a patient. For example, primers for performing RT-PCR, probes for performing northern blot analyses, and/or antibodies for performing proteomic analysis such as Western blot, immunohistochemistry and ELISA analyses can be included in such kits. Appropriate buffers for the assays can also be included. Detection reagents required for any of these assays can also be included. The appropriate reagents and methods are described in further detail below. The kits may include suitable primers and/or probes to detect the expression levels of at least one (up to all) of the genetic modifications disclosed herein. Where expression is determined at the protein level, the kit may contain binding reagents specific for the proteins of interest. The binding reagents may comprise antibodies to include all fragments and derivatives thereof. In the context of the various embodiments of the present invention the term "antibody" includes all immunoglobulins or immunoglobulin-like molecules with specific binding affinity for the relevant protein (including by way of example and without limitation, IgA, IgD, IgE, IgG and IgM, combinations thereof, and similar molecules produced during an immune response in any vertebrate, for example, in mammals such as humans, goats, rabbits and mice). Specific immunoglobulins useful in the various embodiments of the invention include IgG isotypes. The antibodies useful in the various embodiments of the invention may be monoclonal or polyclonal in origin, but are typically monoclonal antibodies. Antibodies may be human antibodies, non-human antibodies, or humanized versions of non-human antibodies, or chimeric antibodies. Various techniques for antibody humanization are well established and any suitable technique may be employed. The term "antibody" also refers to a polypeptide ligand comprising at least a light chain or heavy chain immunoglobulin variable region which specifically recognizes and binds an epitope of an antigen, and it extends to all antibody derivatives and fragments that retain the ability to specifically bind to the relevant protein. These derivatives and fragments may include Fab fragments, F(ab')2 fragments, Fv fragments, single chain antibodies, single domain antibodies, Fc fragments etc. The term "antibody" encompasses antibodies comprised of both heavy and light chains, but also heavy chain (only) antibodies (which may be derived from various species of cartilaginous fish or camelids). In specific embodiments, the antibodies may be engineered so as to be specific for more than protein, for example bi-specific to permit binding to two different target proteins as identified herein (see Tables 2A, 2B and 2C).

In some embodiments, the kits may also contain the specific therapeutic agent to be administered in the event that the test predicts the presence or absence of the genetic modifications disclosed herein. This agent may be provided in a form, such as a dosage form, that is tailored to the specific treatment. The kit may be provided with suitable instructions for administration according to an appropriate treatment regimen.

The kits featured herein can also include an instruction sheet describing how to perform the assays for measuring gene or gene product expression. The instruction sheet can also include instructions for how to determine a reference cohort, including how to determine expression levels of gene or gene product markers in the reference cohort and how to assemble the expression data to establish a reference for comparison to a test patient. The instruction sheet can also include instructions for assaying gene or gene product expression in a test patient and for comparing the expression level with the expression in the reference cohort to subsequently determine the appropriate chemotherapy for the test patient. Methods for determining the appropriate chemotherapy are described above and can be described in detail in the instruction sheet.

Informational material included in the kits can be descriptive, instructional, marketing or other material that relates to the methods described herein and/or the use of the reagents for the methods described herein. For example, the informational material of the kit can contain contact information, e.g., a physical address, email address, website, or telephone number, where a user of the kit can obtain substantive information about performing a gene expression analysis and interpreting the results, particularly as they apply to a human's likelihood of having a positive response to a specific therapeutic agent.

The present invention will be further illustrated in the following Examples which are given for illustration purposes only and are not intended to limit the invention in any way.

EXAMPLES

Example 1

Study Oversight

The study was performed in accordance with protocols approved by the institutional review board at the Dana-Farber/Harvard Cancer Center. All patients provided written informed consent for the genetic research studies and molecular testing.

Patients and Tumor Samples

Figure 8:
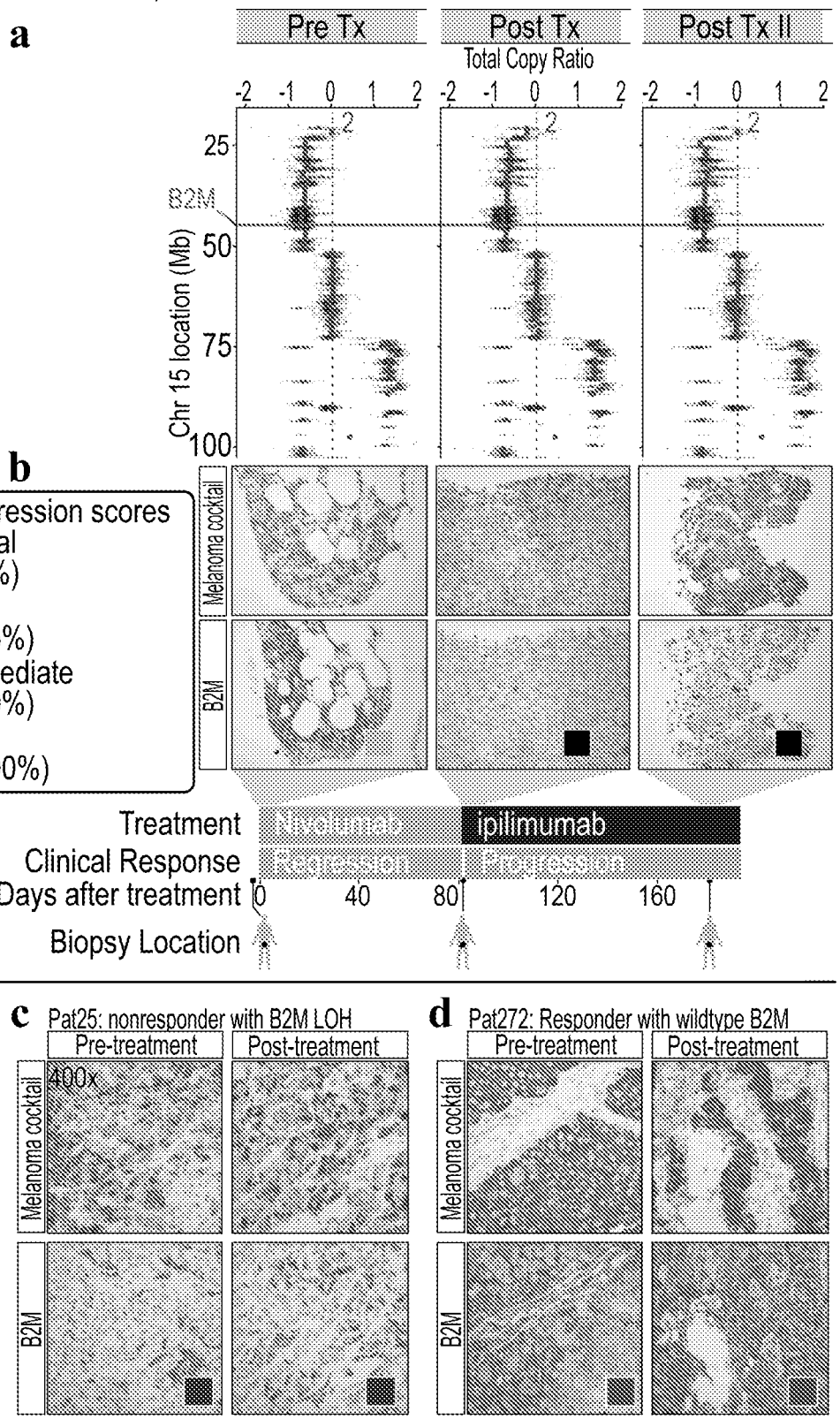
FIG. 8 is a set of data and corresponding images showing LOH in B2M is found in resistance and non-responding patients treated with CPB. (a) Illustration of the deletions locations on chromosome 15 overlapping the B2M locus found in Pat99 (blue line); and the total copy ratios of target regions on chromosome 15 in each biopsy. Red dashed lines indicate an absolute total copy number of 2 as inferred by ABSOLUTE. A deleted region overlapping the B2M locus is seen in all samples. Top row indicates the timeline of treatment (blue-regression, orange-progression). (b-d) Samples from Pat99 (b), Pat25 (c) and Pat272 (d) were stained with an antibody cocktail for melanoma cells (mel.cocktail) using anti-melanosome (HMB45), anti-MART-1/melan A and anti-Tyrosinase, to discern melanoma cells from normal cells; or with an antibody specific for B2M. Colored boxes indicate B2M expression scores: B2M scoring was estimated by using 4 different levels of expression in the tumor fraction: Minimal—0-10%; Low—10-50%; Intermediate—50-80%; and High—80-100%, B2M expression in the tumor fraction. Original Magnification ×100.

Patients with metastatic melanoma provided written informed consent for the collection of tissue and blood samples for research and genomic profiling, as approved by the Dana-Farber/Harvard Cancer Center Institutional Review Board (DF/HCC Protocol 11-181). Matched tumor and normal blood samples were obtained from patients before treatment and at the time of and after disease progression. Samples were removed from the following location—Pat208: right anterior lower leg pre-ipilimumab therapy (Pre Tx); right distal anterior thigh during disease regression at 42 days after the start of treatment (Post Tx); right anterior lower leg at time of progression, 182 days post-ipilimumab and at the beginning of nivolumab therapy (2 lesions, Post Tx II 1 and Post Tx II 2); right distal anterior thigh at 245 days post-nivolumab (Post Tx III); and right anterior knee at 343 days post-nivolumab (Post Tx IV) (FIG. 2A). Pat33: skin right leg pre-durvalumab treatment (Pre Tx); skin, right side on right leg at 17 days after the start of Durvalumab (Post Tx); and right semi pelvis, 344 days after the start of durvalumab (Post Tx II). Pat99: skin left groin 2 days prior to the start of nivolumab (Pre Tx); skin left groin 83 days after the start of nivolumab and at the beginning of ipilimumab treatment (Post Tx); and skin left groin 182 days after the start of nivolumab treatment (Post Tx II) (FIG. 8B).

Sample Processing

DNA was extracted using Qiagen AllPrep DNA/RNA Mini Kit (cat #80204) from fresh frozen tumor samples and stored at −80° C. Germline DNA was extracted from matched peripheral mononuclear cells.

Whole Exome Sequencing

Whole exome sequencing from DNA extracted from fresh frozen tumors and matched normal blood samples was done as previously described[25,26]. All procedures were done at the Genomics Platform of the Broad Institute of Harvard and MIT.

Library construction: DNA input used for generation of libraries was 250-500 ng in 100 μl of TE buffer. For adaptor ligation palindromic forked adapters (Integrated DNA technologies) with unique 8 base index molecular barcode sequences included in the adapter sequence to enable pooling of all samples. All other reagents used for end repair, A-base addition, adapter ligation and library enrichment PCR were purchased from KAPA Biosciences in 96-reaction kits. After the post library enrichment process, solid phase reversible immobilization (SPRI) beads cleanup (Beckman Coulter, cat #A63881) were used to reduce the volume to 20 μl to maximize library concentration. An automated PicoGreen assay on an Agilent Bravo instrument was done to measure libraries concentrations, all libraries above 40 ng/μl were considered acceptable for solution-phase hybrid selection and sequencing.

Solution-phase hybrid selection and capture protocol: Hybridization of samples was done by using whole exome baits (Agilent SureSelect Human All Exon Kit v2) as previously described[27]. Hybridization was carried out by denaturing the samples for 95° C. for 5 minutes followed by incubation for 17 hours at 65° C. on an Eppendorf Mastercycler Pro Thermal cycler. Capture of DNA-RNA complexes was performed using the Agilent Bravo instrument. The reaction was carried out, using the SureSelect Target Enrichment System Sequencing Platform Library Prep v2 (Agilent Technologies, cat #G3360-90000), according to manufacturer's specifications.

Preparation of libraries for cluster amplification and sequencing: Libraries were quantified and normalized using PicoGreen to ensure equal concentration using a Perkin Elmer Mini Janus instrument and pooled by equal volume on the Agilent Bravo instrument. Next, library pools were quantified using quantitative PCR (KAPA Biosystems, cat #KK4832) with probes specific to the ends of the adapters. After qPCR, libraries were brought to 2 nM and denatured using 0.2M NaOH on the Perkin Elmer MiniJanus. After denaturation, libraries were diluted to 20 pM using hybridization buffer (Illumina).

Cluster amplification and sequencing: Cluster amplification of denatured templates was performed according to the manufacturer's protocol (Illumina), HiSeq 2500 v4 cluster chemistry and flowcells, as well as Illumina's Multiplexing Sequencing Primer Kit. Libraries were sequenced using the HiSeq 2500 v4 Sequencing-by-Synthesis method followed by analysis with RTA v.1.12.4.2. Each pool of whole exome libraries was subjected to paired 76 bp runs. An 8 base index sequencing read was used to read molecular indices, across the number of lanes needed to meet coverage for all libraries in the pool.

Sequencing quality control: Quality control modules using the Broad Institute Genome Analysis pipeline Firehose (www.broadinstitute.org/cancer/cga/Firehose) were applied to all sequencing data for comparison of the origin for tumor and normal genotypes and to assess fingerprinting concordance.

Sanger Sequencing: Genomic DNA extracted from patients samples was used to validate the WES c.(37-39)ctcfs, p.Leu13fs; and c.(40-45)tctcttfs, p.Ser14fs mutations found in Pat208 and Pat33 by using targeted Sanger sequencing. After DNA isolation, exon-1 in chromosome 15, where the two mutations are located was amplified using primers B2M_F (GGCATTCCTGAAGCTGACA) (SEQ ID No: 2) and B2M_R (GAAGTCACGGAGCGAGAGAG) (SEQ ID No: 3), followed by standard PCR conditions (95° C. 10 minutes; ×35 cycles [95° C. 30 seconds, 58° C. 15 seconds, 72° C. 15 seconds]; 72° C. 5 minutes, 4° C. ∞), using Platinum PCR Supermix (Invitrogen, cat #12532-016). Sanger sequencing was done using the B2M_R primer and was compared to normal control sample for each patient as a negative control.

Analysis of Whole Exome Sequencing

Sequencing data processing: Whole exome sequencing data was processed via two computational pipelines in sequence. First, raw sequencing data from Illumina HiSeq was processed in Picard, a tool developed by the Genomics Platform at the Broad Institute. For each tumor or normal sample, Picard checks for contamination, aligns reads to the reference genome (hg19), and calculates quality metrics, resulting in a single de-multiplexed, aggregated file in the BAM format (see, samtools.github.io/hts-specs/SAMv1.pdf). Second, the BAM files were processed using the Cancer Genome Analysis pipeline, also known as "Firehose". Firehose takes paired BAM files from one tumor and one matched peripheral blood samples, and performs various functions, including quality control, local realignment, detection of somatic single-nucleotide variants (SSNVs) and somatic copy number alterations (SCNAs), and others. Processing details involving Firehose have been detailed elsewhere (see, www.broadinstitute.org/cancer/cga)[28,29].

Mutation calling: SSNVs, insertions and deletions (INDELs) were called using Mutect2[30]. SSNVs within coding regions of the genome were annotated for chromosomal location, variant type, genome change, codon change, and protein change using Oncotator[31]. All mutations called in B2M were manually verified in IGV[28]. Various quality controls were used to filter out artifacts due to formalin fixation or oxidation during library preparation. SCNAs were detected using Recapseg[31], and allele-specific copy number variation was detected using Allelic Capseg. Both tools are available on Firehose.

Cancer cell fraction, ploidy, and power calculation: Due to variable tumor fraction of biopsies, it is important to normalize the variant allele frequency (VAF), defined as the frequency at which a variant is seen out of the total number of reads at a position, to cancer cell fraction (CCF), the estimated fraction of cancer cells containing the variant. ABSOLUTE[32] was used to infer CCF values for SSNVs and INDELs. In addition, ABSOLUTE also calculated ploidy, purity, and absolute DNA copy numbers of SCNAs. The power to detect events given sample purity and coverage was calculated by ABSOLUTE.

Phylogenetic Reconstruction

PhyloWGS[33] was used to reconstruct complete genotypes and phylogenetic relationships of tumor subpopulations from CCF values of SSNVs, INDELs, and SCNAs. PhyloWGS is capable of performing on both WES as well as whole genome sequencing data (github.com/morrislab/phylowgs/issues/12). PhyloWGS separates variants into simple somatic mutations (SSMs) and copy number variations (CNVs). It corrects SSM frequencies in regions overlapping CNVs, and models CNVs as pseudo-SSMs. PhyloWGS is based on a generative probabilistic model. SSMS and CNVs are clustered using the non-parametric Dirichlet process prior. The clonal evolutionary structure is modeled with the tree-structured stick-breaking process prior. PhyloWGS then uses the Metropolis-Hastings algorithm, a Markov chain Monte Carlo (MCMC) procedure, to sample phylogenies from the model posterior that are consistent with SSM frequencies and evolutionary constraints.

For patients with more than 1,000 mutational events, SSNVs and INDELs were clustered in PhyloWGS without SCNAs. CCF values were normalized by respective read depths and used as variant frequencies for input into PhyloWGS. Results for Pat208 required manual curation due to the PhyloWGS algorithm's propensity for designating p.Leu13fs as the parent of p.Ser14fs, in violation of the "crossing rule" outlined in the PhyloWGS paper as well as the ample evidence for a sibling relationship between the two mutations. Thus, confidence for p.Ser14fs were artificially inflated by multiplying both the alternate and reference counts for the corresponding SSM by 1000. The resulting subtree rooted at the population containing p.Ser14fs was then merged back onto the original PhyloWGS output as a sibling of the subtree rooted at the population containing p.Leu13fs. All events assigned to the new subtree rooted at the population containing p.Ser14fs were then removed from other populations elsewhere in the tree such that no event was represented more than once.

Calculation of Neoantigen Load

POLYSOLVER (POLYmorphic loci reSOLVER) was used to infer the HLA type for each patient, using sequencing data from the matched peripheral blood sample[34]. Potentially antigenic peptide sequences were inferred from mutational data. Neoantigen binding predictions were made using NetMHCPan[35]. Peptides were designated as strong binders (mutant peptide with higher affinity than 0.5% of random natural peptides, with corresponding wildtype peptide having lower affinity than 2% of random natural peptides) or weak binders (mutant peptides with higher affinity than 2% of random natural peptides, with corresponding wildtype peptide having lower affinity than 2% of random natural peptides) with respect to the patient's inferred HLA type. Mutated genes predicted to give rise to at least one neoantigen were used to calculate the neoantigen load.

Visualization of TCGA Data

Lollipop plots of B2M mutations found in TCGA datasets were visualized using cbioportal (www.cbioportal.org/), using the web query interface[36,37].

Histology and Staining

IHC staining: Immunohistochemistry staining was performed on 4 micrometer formalin-fixed paraffin-embedded sections. All procedures were done on the automated Ventana Discovery Ultra staining system. Sections were first deparaffinized with xylene and alcohol series, treated with EDTA retrieval solution and blocked with Discovery inhibitor (Ventana products). Sections were incubated with primary antibodies for 16 minutes, washed and incubated with a secondary antibody conjugated with horseradish peroxidase (HRP) for additional 16 minutes. Discovery purple chromogen kit (Ventana, cat #760-229) was then applied to generate a color reaction. Slides were then counterstained with hematoxylin (Ventana). Primary antibodies used for staining were: anti-B2M (Abcam, cat #ab27588; 1:1000) and anti-melanoma triple cocktail (HMB45+A103+T311; Ventana, cat #790-4677) containing the following antibodies: anti-Melanosome (HMB45), anti-MART-1/melan A (A103), and anti-Tyrosinase (T311). Protocols for B2M and the melanoma triple cocktail staining are summarized in (Table 1).

Scoring B2M Expression in the Tumor Cells

Figure 10:
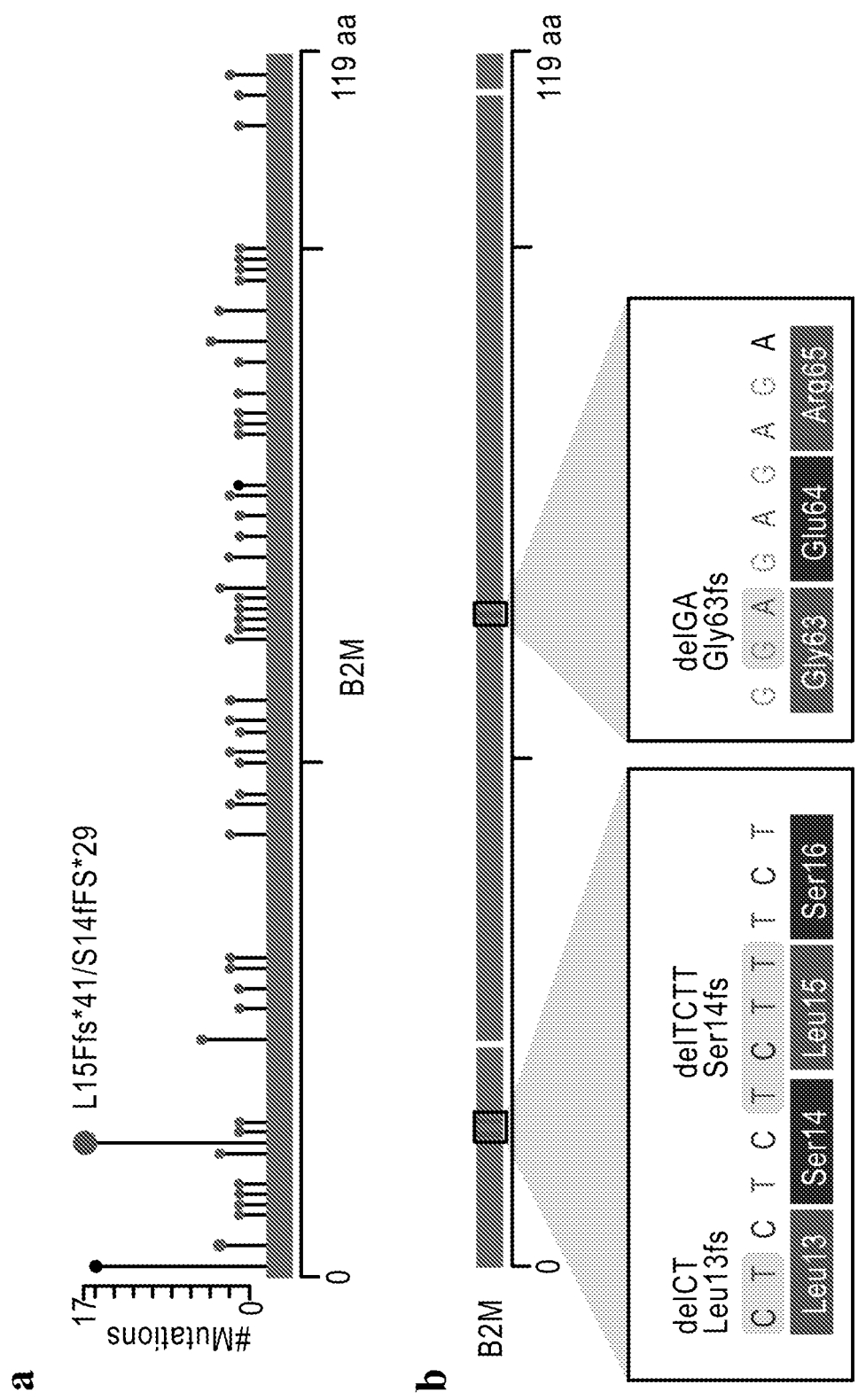
FIG. 10 illustrates that B2M mutational hotspots seen in TCGA data lie within 4× dinucleotide repeats. Long blue rectangles indicate exons of B2M. (a) The number of B2M mutations found in TCGA along B2M exons. A hotspot at p.Leu15 and p.Leu14 is labeled. (b) B2M mutations found in Pat208 and PatT33. Insets display the DNA sequence and amino acids at boxed locations, showing 4× dinucleotide repeats (SEQ ID No: 1).
Figure 11:
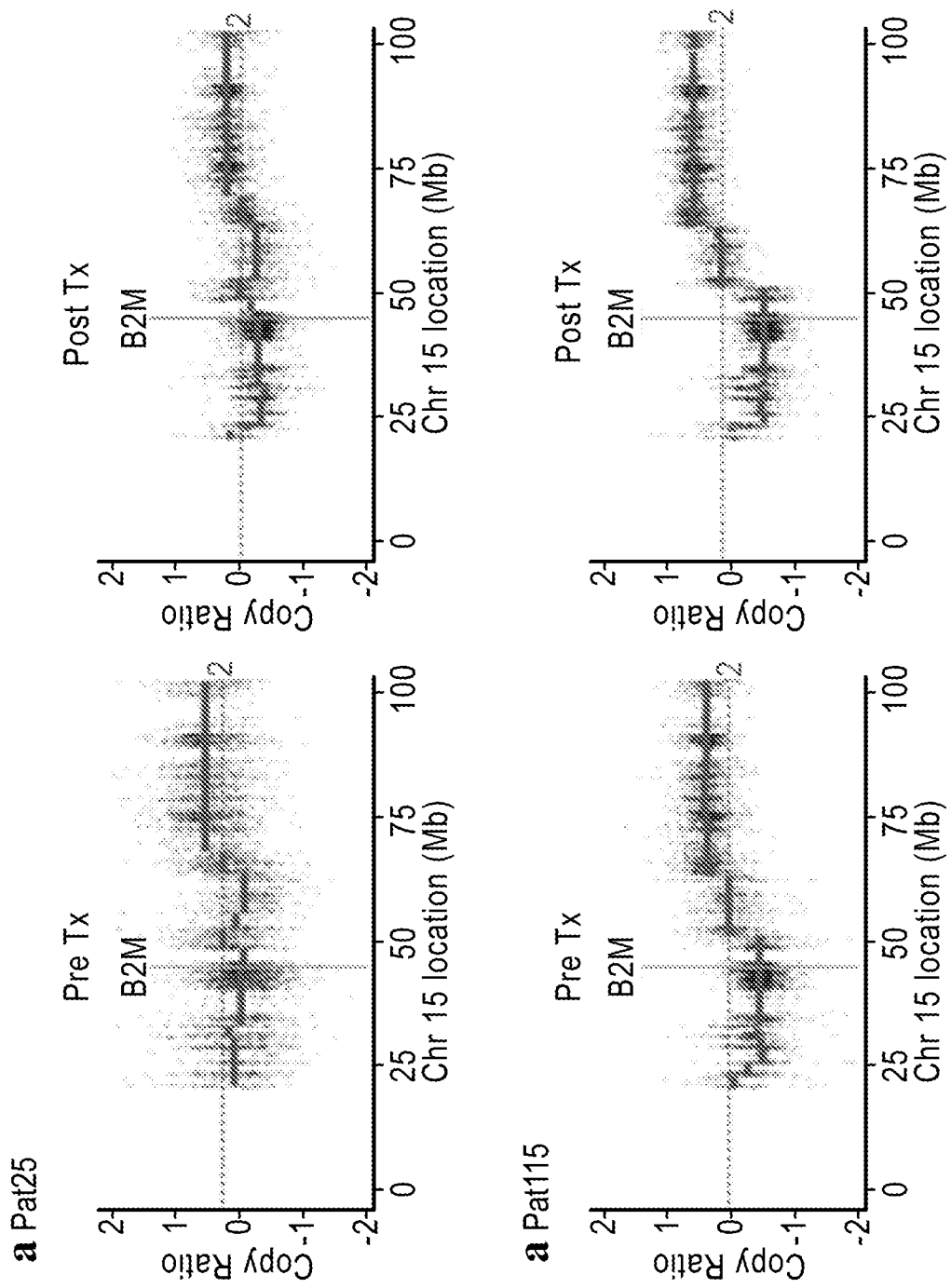
FIG. 11 illustrates that total copy number from biopsies taken from non-responders shows a deletion overlapping the B2M locus. (a-b) Results from ReCapSeg of pre-CPB and post-CPB biopsies from two non-responders, Pat25 (a) and Pat115 (b), are shown. The horizontal axis indicates position on chromosome 15. The vertical axis indicates the total copy number ratio of targets. Each dot indicates a target region used to calculate copy ratio information. Solid red horizontal lines are segments inferred by the ReCapSeg algorithm. Dashed red lines indicate copy ratio corresponding to a total copy number of two, as inferred by ABSOLUTE.
Figure 12:
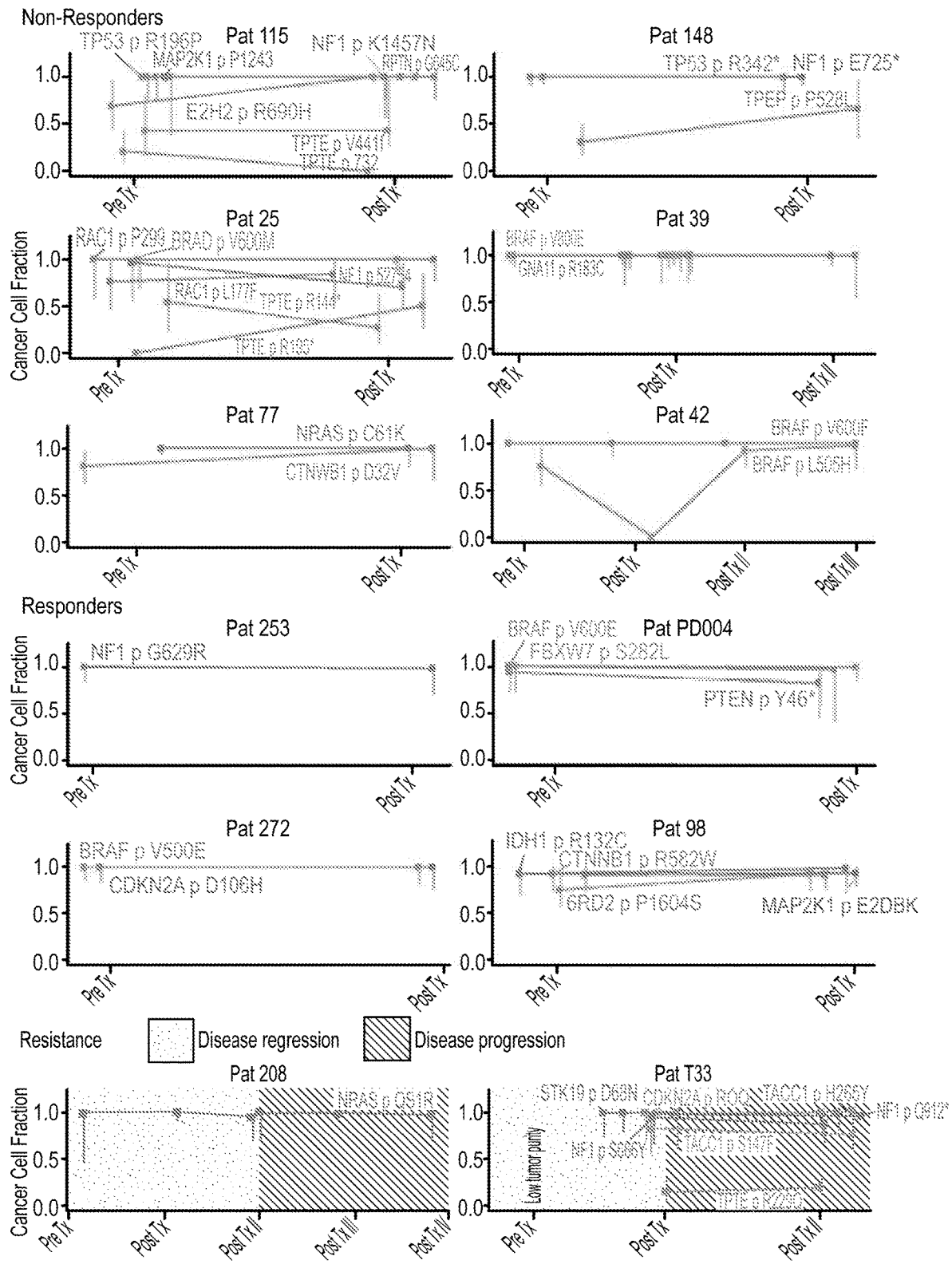
FIG. 12 illustrates that the cancer cell fraction (CCFs) of most known melanoma drivers did not change significantly over time in tumor biopsies. Panels display CCF values for known melanoma drivers in 12 patients out of 17. No known melanoma related drivers were detected in Pat155, Pat62, Pat51, Pat99 and Pat131.
Figure 13:
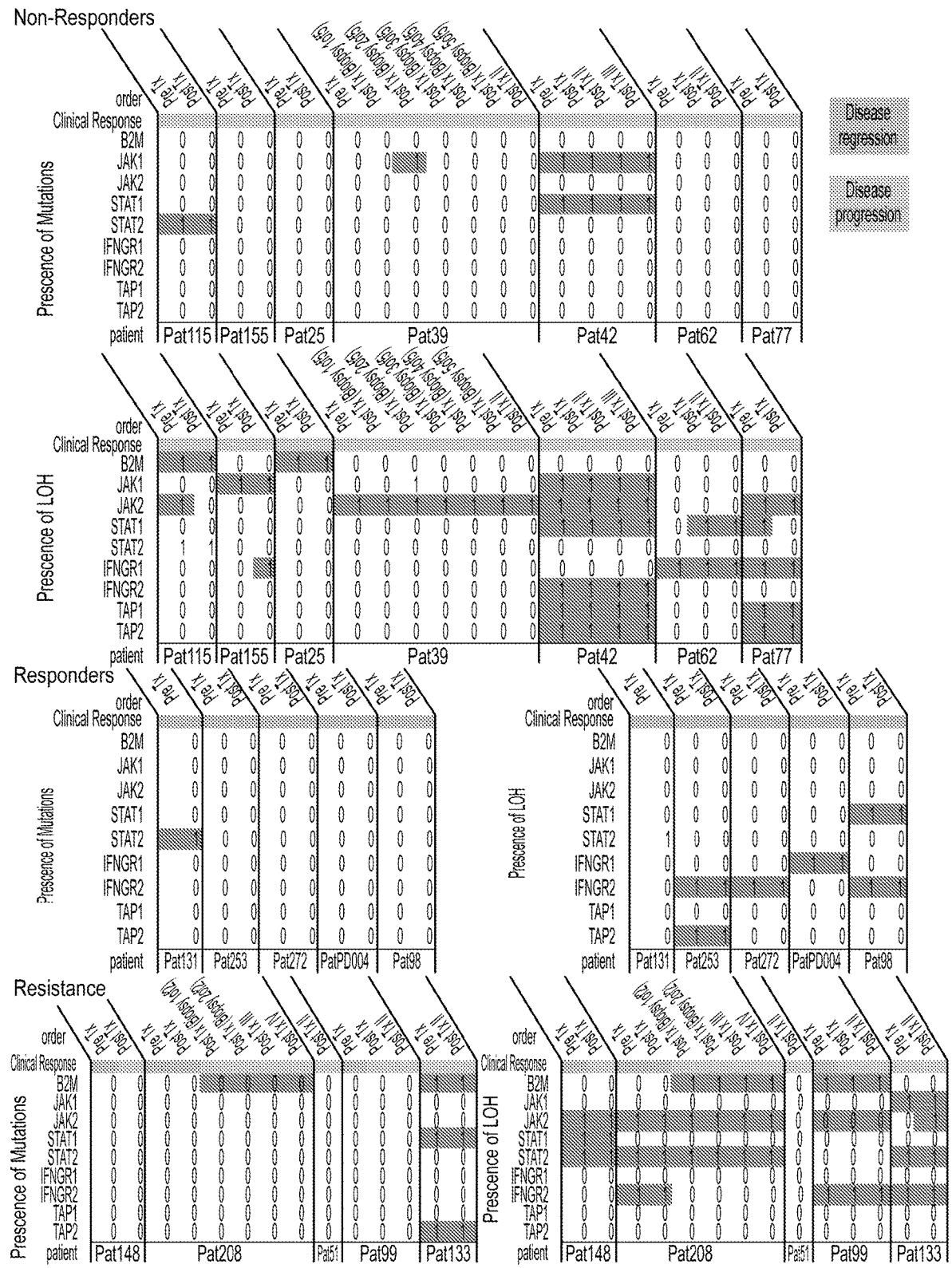
FIG. 13 illustrates a summary of genetic aberrations in antigen presentation machinery related genes. 1 and 0 indicate the presence and absence of an aberration, respectively. Samples with low tumor purity were not included. Columns indicate samples and are grouped by patients. Rows indicate genes. Patients are grouped by phenotype. Note a copy number-neutral LOH is seen in Pat208 Pre Tx and Post Tx.
Figure 14:
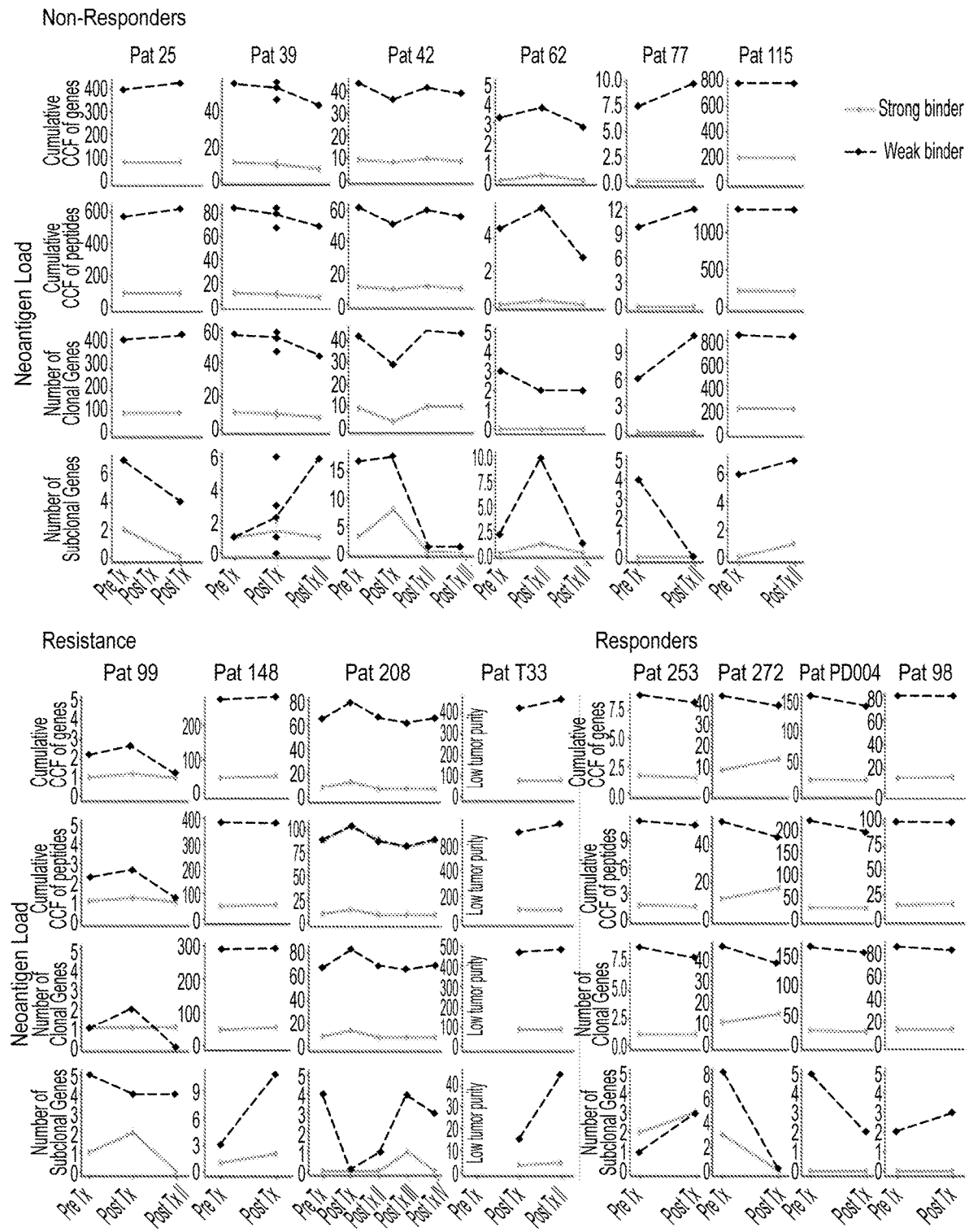
FIG. 14 illustrates neoantigen load in patients treated with CPB. Each plot displays the neoantigen load over time per patient. For each patient, in the top row, CCF values for genes that contributed at least one neoantigen were summed. In the second row, CCF values for each predicted antigenic peptide was summed, such that genes contributing multiple neoantigens would be represented multiple times. In the third row, the number of clonal genes that contributed at least one neoantigen was calculated. In the last row, the number of subclonal genes that contributed at least one neoantigen was calculated. Red lines indicate strong binders, blue lines indicate weak binders.

The anti-melanoma triple cocktail was used to discern melanoma cells from normal cells, allowing B2M expression levels to be estimated for only the cancerous cell fraction. A single-blind scoring of cancer-specific B2M expression was conducted by 2 pathologists at Massachusetts General Hospital. B2M scoring was estimated by using 5 different levels of expression in the tumor fraction: NT—no tumor; Minimal—0-10%; Low-10-50%; Intermediate—50-80%; and High—80-100% B2M expression in the tumor fraction (FIG. 10 and FIG. 11).

TABLE 1

IHC protocol summary.

|  | Beta-2 Microglobulin | mel.cocktail |
|---|---|---|
| Deparafinization | 70 C., 24 minutes | 70 C., 24 minutes |
| Antigen retreival | 90 C. 32 minutes | 91 C. 32 minutes |
| eHRP inhibition | 8 minutes | 8 minutes |
| Primary Antibody | 36 C., 16 minutes | 36 C., 16 minutes |
| Secondary Antibody | RT, 16 minutes | RT, 16 minutes |
| Purple staining | 12 minutes | 12 minutes |
| Hematoxylin | 8 minutes | 8 minutes |
| Blueing reagent | 8 minutes | 8 minutes | eHRP—endogenous horseradish peroxidase
RT—room tempature

Example 2

Results

A deeper understanding of the mechanisms underlying response and resistance to checkpoint blockade (CPB), coupled with effective clinical diagnostics, would enable better therapeutic strategies to induce long-term responses and earlier detection of progressive disease. To date, several clinical predictors of CPB response in melanoma have been identified, but currently are not being used to select patients for therapy. Additionally, mutations in Janus kinase 1 and 2 (JAK1, JAK2) were recently implicated as drivers of resistance in two melanoma patients treated with anti-PD-1[39]. Despite these advances, CPB resistance mechanisms remain incompletely characterized and have yet to be validated in large cohorts.

Figure 2:
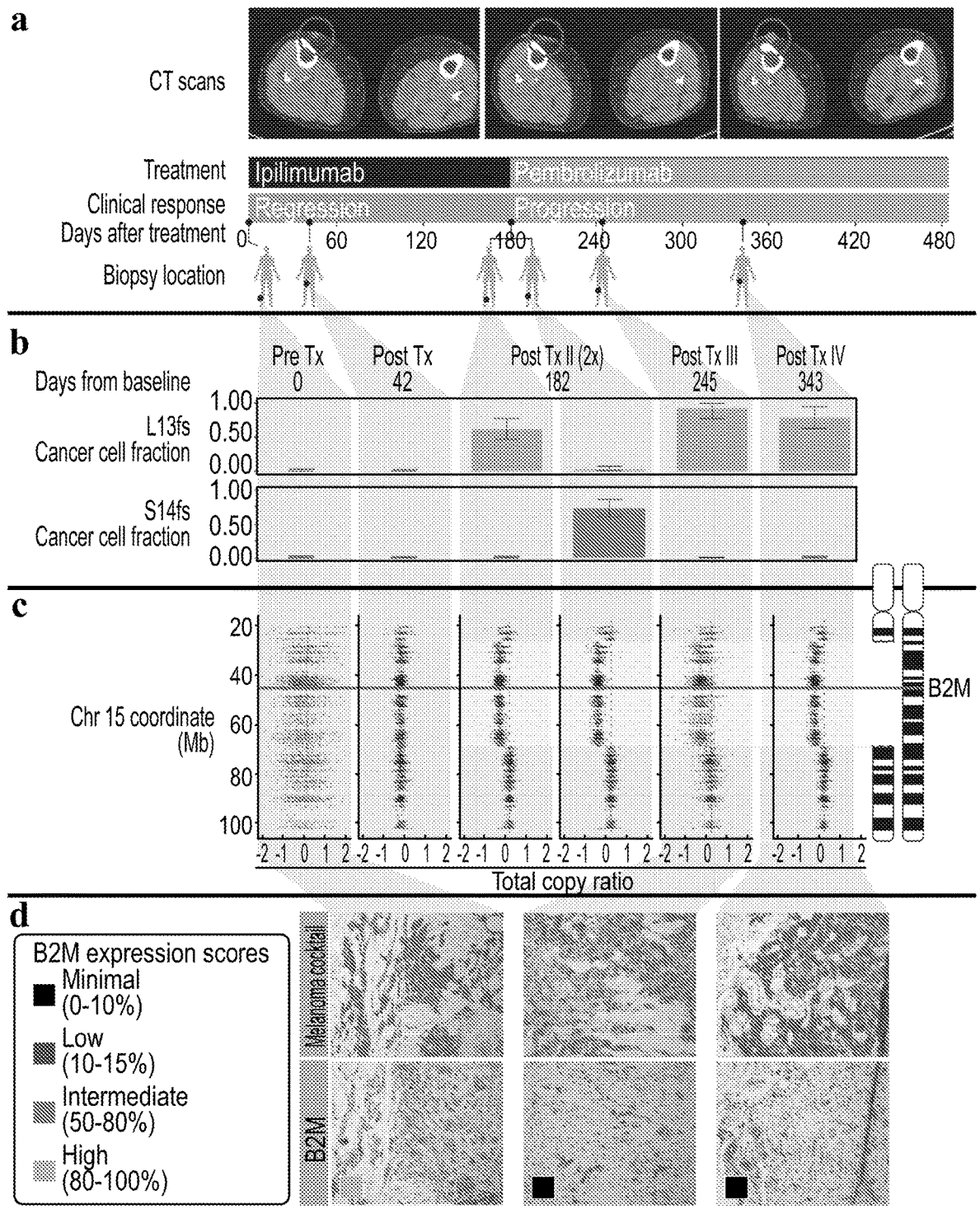
FIG. 2 provide sets of images and data showing that loss of B2M is associated with resistance in a patient treated with checkpoint blockade. (a) Treatment and sample collection timeline for Pat208. Row 1, computed tomographic (CT) images of right thigh taken at baseline, during response and relapse; row 2, CPB treatments (ipilimumab-anti-CTLA4, pembrolizumab-anti-PD-1): row 3, clinical response while on treatment, with blue indicating regression and orange indicating progression; row 4, days elapsed with respect to the start of treatment; row 5, location of biopsies taken at the different time points. (b) Fraction of cancer cells harboring two separate early frameshift mutations in B2M (p.Leu13fs and p.Ser14fa) detected in Pat208. Blue backgrounds indicate samples taken during disease regression, and orange backgrounds indicate samples taken during disease progression. Error bars indicate 95% confidence intervals as inferred by ABSOLUTE described below. (c) Illustration of the deletions locations on chromosome 15 overlapping the B2M locus found in Pat208, as well as the location of the two early frameshift mutations relative to the B2M gene (blue line); and the total copy ratios of target regions on chromosome 15 in each biopsy. Red dashed lines indicate an absolute total copy number of 2 as inferred by ABSOLUTE. A deleted region overlapping the B2M locus is seen in all relapse samples (light orange background). (d) Samples were stained with an antibody cocktail for melanoma cells (mel.cocktail) using anti-melanosome (HMB45), anti-MART-1/melan A and anti-Tyrosinase, to discern melanoma cells from normal cells; or with an antibody specific for B2M. Colored boxes indicate B2M expression scores; B2M scoring was estimated by using 4 different levels of expression in the tumor fraction: Minimal—0-10%; Low—10-50%; Intermediate—50-80%; and High—80-100%, B2M expression in the tumor fraction. Original magnification ×100.

To identify additional genomic mechanisms of acquired resistance, whole exome sequencing was performed on 49 matched longitudinal tumor and blood samples from 17 patients with metastatic melanoma, 10 of whom initially responded to CPB, with five eventually succumbing to disease progression. Of these five patients, one (Pat208) showed a response lasting more than six months and had a total of six high quality biopsies at baseline, disease regression, and disease progression (FIG. 2). Three of the patients with metastatic melanoma that exhibited acquired resistance to CPB therapy are further described (summarized in Table 2).

TABLE 2

Clinical parameters.

| | Pat208 | Pat33 | Pat99 |
|---|---|---|---|
| Age | 84 | 60 | 61.5 |
| Gender | F | F | M |
| Stage | IIIC | IV-M1c | IV-M1c |
| LDH | 221 | NA | 192 |
| Mutation in melanoma related drives | NRAS p.Q61R | NF1 p.Q912* NF1 p.S666Y TPTE p.R229Q STK19 p.D89N CDKN2A p.R0Q TACC1 p.S147F TACC1 p.H265Y | NA |
| Therapy | Ipilimumab Pembrolizumab | MEDI4736 | Nivolumab Ipilimumab |
| Duration of regression (months) | 6 | 2.3 | 2.6 |
| Overall survival (Days) | 1022 | 650 | 900 |
| B2M mutations | Deletion B2M p.Leu13fs B2M p.Ser14fs | B2M p.Gly63fs B2M p.Ser14fs | Deletion |
| IHC score | Pre Tx- High Post Tx- NT Post Tx II-NT Post Tx III- Minimal Post Tx IV- Minimal | Pre Tx- NT Post Tx- Minimal Post Tx II- Minimal | Pre Tx- High Post Tx- Minimal Post Tx II- Minimal |

NA—not applicable (data not available);
F—female,
M—male
IHC score: NT—no tumor; Minimal—0-10%; Low—10-50%, Intermediate—50-80%; High—80-100% (percentages reflect B2M expression in the tumor fraction)

Pat208—A 84-year-old woman with unresectable stage IIIC melanoma positive for NRAS mutation received 4 doses of ipilimumab (anti-CTLA4 antibody) 3 mg/m$^2$ every 3 weeks. First restaging imaging 12 weeks post-therapy initiation showed regression of many in-transit lesions. Repeat imaging 8 weeks later showed unambiguous disease progression. Ipilimumab was discontinued, and she began treatment with pembrolizumab (anti-PD1 antibody), 2 mg/kg every 3 weeks, 7 cycles total. Imaging was performed 12 weeks after pembrolizumab initiation. Treatment was discontinued 3 cycles after imaging, following obvious clinical progression (FIG. 2A).

Pat33—A 60-year-old woman diagnosed with stage-IV-M1C melanoma of unknown primary, positive for NF1 mutation, was initially treated with systemic therapy with high-dose interleukin-2 (IL2) that was associated with regression of hepatic diseases and stability in the lungs, right adrenal, and spleen. Following 2 years of disease regression/stability, imaging showed progression in several lesions. In 2013, after 6 years without any systemic therapy, the patient received four doses of ipilimumab, 3 mg/m$^2$ every 3 weeks. Patient had no response to ipilimumab, and successive imaging over a one-year period showed slow growth of her pelvic disease. She then commenced therapy with durvalumab (anti-PD-L1 antibody) 10 mg/kg every 2 weeks, and had regression of her disease lasting over 2.3 months. After that time point, the patient's disease progressed, though she remained on treatment until a right hemipelvectomy was performed approximately 10 months after starting treatment.

Pat99—A 61-year-old male with stage IV-M1C metastatic mucosal melanoma (urethral) initially received high-dose IL2 therapy and had evidence of disease progression on first post-treatment imaging. He then commenced therapy with nivolumab (anti-PD1 antibody) 3 mg/kg every 2 weeks for 10 weeks, and had evidence of disease regression that lasted for 2.6 months. He then received 2 doses of ipilimumab 3 mg/m$^2$ every three weeks. However, treatment was discontinued due to development of treatment-related colitis that was soon followed by obvious clinical progression (FIG. 8b). After recovery, he restarted nivolumab until imaging showed unequivocal disease progression based on the rapid growth of a left-sided mesenteric mass.

Figure 3:
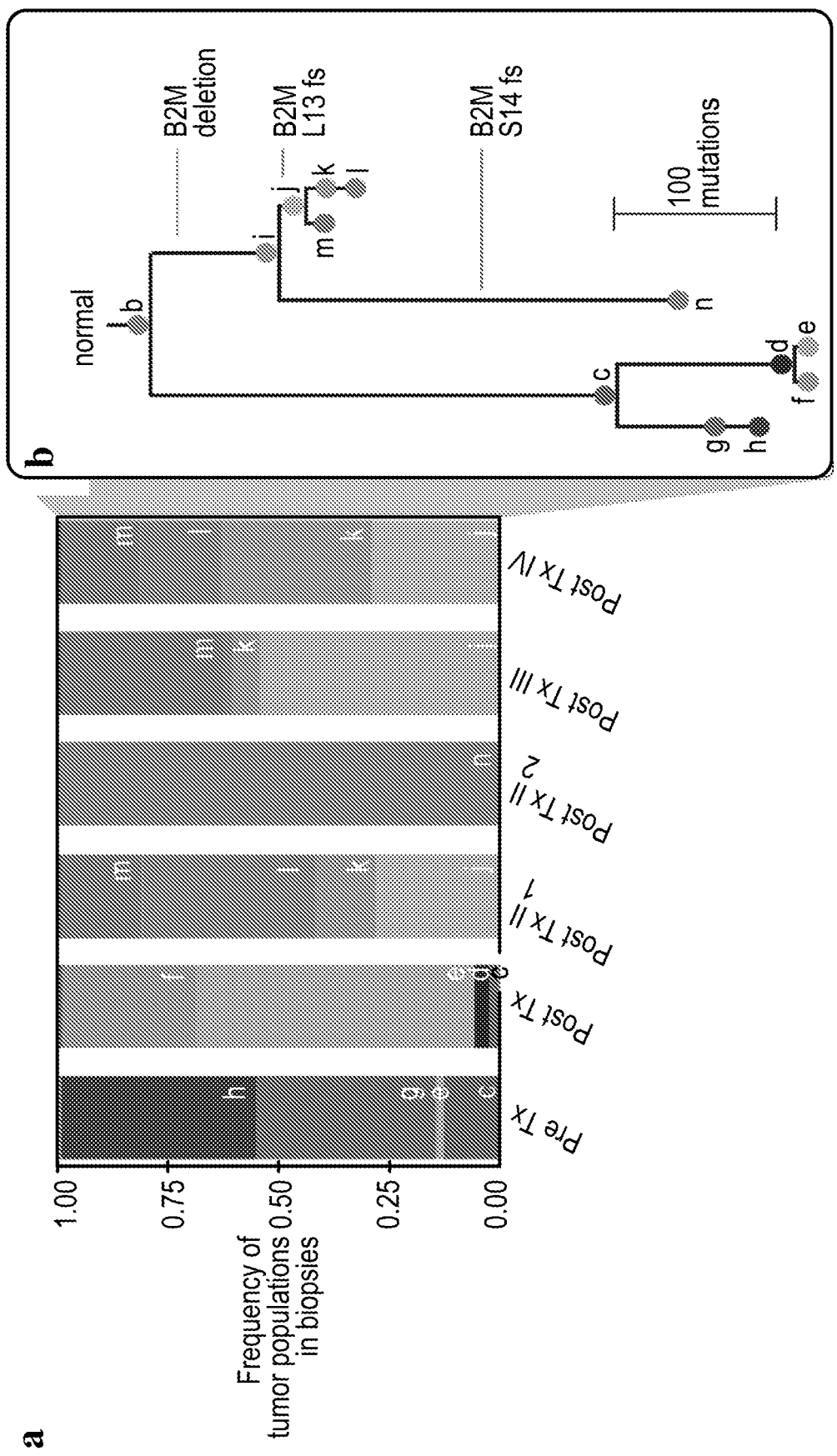
FIG. 3 is a set of graphs with (a) showing subclonal composition of each biopsy as inferred by phyloWGS (described below). Each color indicated a separate population in the tumor. (b) Shows the phylogenetic relationships between populations shown in (a).

To identify potential drivers of resistance in Pat208, we looked for genes with multiple non-silent mutations and loss of heterozygosity (LOH) that were dominant only during progressive disease. Of 5,761 mutations found, only B2M mutations satisfied all criteria (FIG. 2b). Two frameshift mutations were found in exon 1 of B2M: p.Leu13fs and p.Ser14fs. The presence of these mutations was confirmed only during progression by targeted Sanger sequencing and manual review of sequenced reads at the B2M locus. As expected by the nature of CPB, no significant changes were found in melanoma drivers[11] Chromosome 15 segment copy ratios show similar break points in all progression samples of Pat208, indicating a single B2M deletion event preceding the acquisition of p.Leu13fs and p.Ser14fs (FIG. 2c). Due to this LOH and early frameshift mutations in B2M, the majority of cancer cells in progression samples appeared to be B2M-deficient (FIG. 3a,b).

To explore whether genetic alterations in B2M led to loss of protein expression, immunohistochemistry (IHC) was performed on Pat208 biopsies. As expected from the identified B2M frameshift mutations, a dramatic drop in tumor-specific B2M protein levels occurred after Pat208 developed resistance (FIG. 2d).

The spatial distribution and population frequency of the two B2M mutations suggest that a tumor lineage diverged early, developed B2M LOH, and branched into two separate CPB-resistant populations, each with a distinct early frameshift in B2M. Despite the spatial proximity of Post-Tx-II-1 and Post-Tx-II-2 (FIG. 2a), p.Ser14fs was only detected in Post-Tx-II-2 (73% of cancer cells) and not Post-Tx-1 (0%). In contrast, p.Leu13fs was high only in Post-Tx-II-1 (62%) but not in Post-Tx-II-2 (3%) (FIG. 2b). Phylogenetic reconstruction using all mutations found in Pat208 biopsies resulted in two major lineages branching early in the tumor's evolutionary history. Biopsies taken before progressive disease were composed of lineages on the left branch, while biopsies taken after progressive disease were composed of lineages on the right branch (FIG. 3a,b). While this pattern could be attributed to spatial heterogeneity of lesions, the absence of lineages from the left branch of the tree in all four progression biopsies and the dominance of new B2M-deficient lineages suggest that B2M loss led to significant selective advantages.

Although several genes are responsible for the processing, loading, and presentation of antigens, and have been shown to be mutated in cancers[21], no proteins can substitute for B2M in HLA class I presentation, making the loss of B2M presence an evolutionary attractive route for CPB resistance[10]. While B2M aberrations are rare in melanoma (1.7-4% of cases)[11,12,13,] B2M loss has been hypothesized as a mechanism of immune escape in some cancers, although only recently in the context of CPB[39,14-17]. Furthermore, while JAK1 and JAK2 were recently implicated as drivers of CPB resistance[39] (in 2 out of 15 patients with an objective response followed by disease progression), only JAK1 mutations were observed in two non-responders, and no JAK2 mutations were found.

Figure 4:
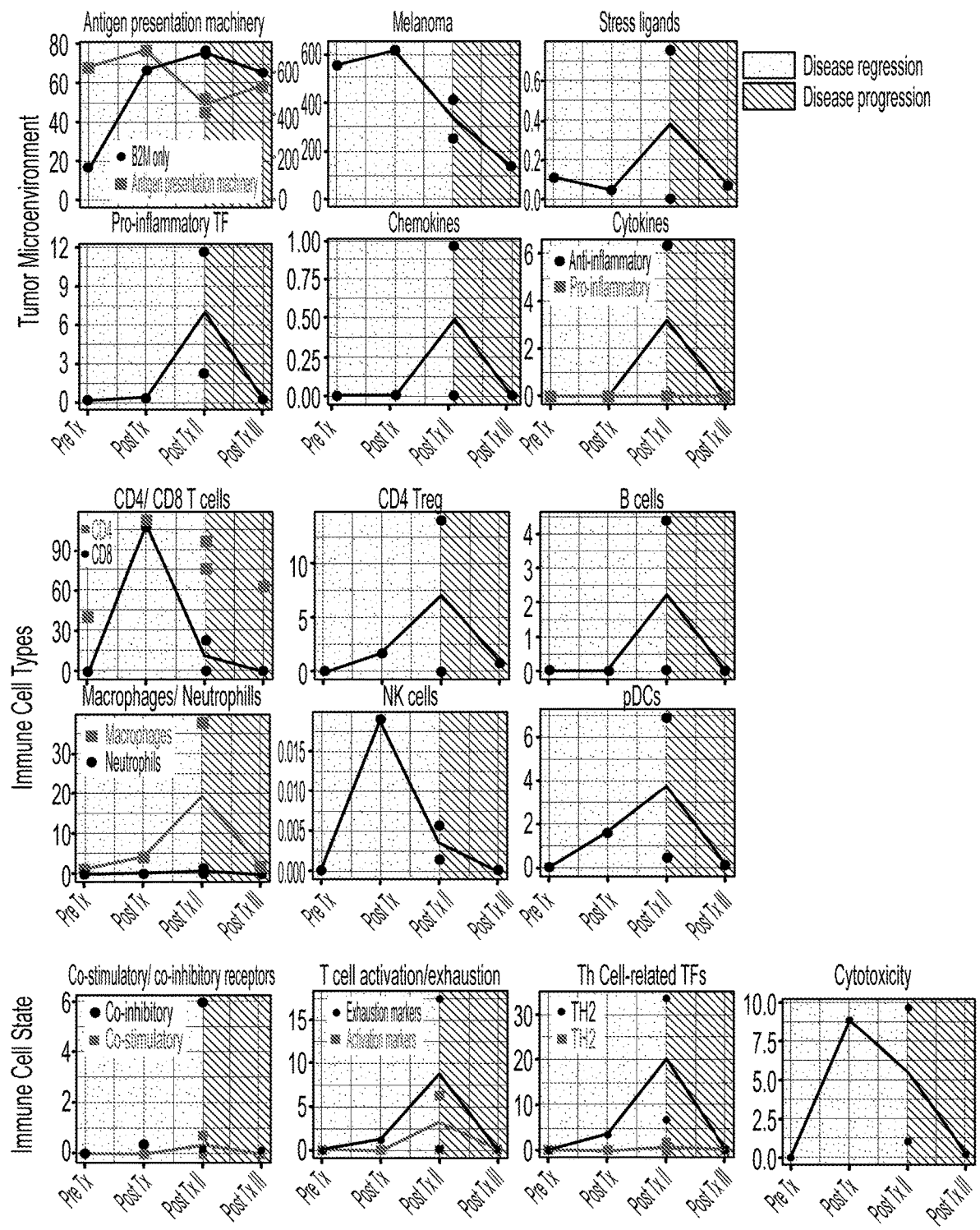
FIG. 4 is a set of expression scores of genes related to the tumor microenvironment, immune cell types, or immune cell states. Blue backgrounds indicate biopsies taken during disease regression, and orange backgrounds indicate biopsies taken during disease progression.
Figure 5:
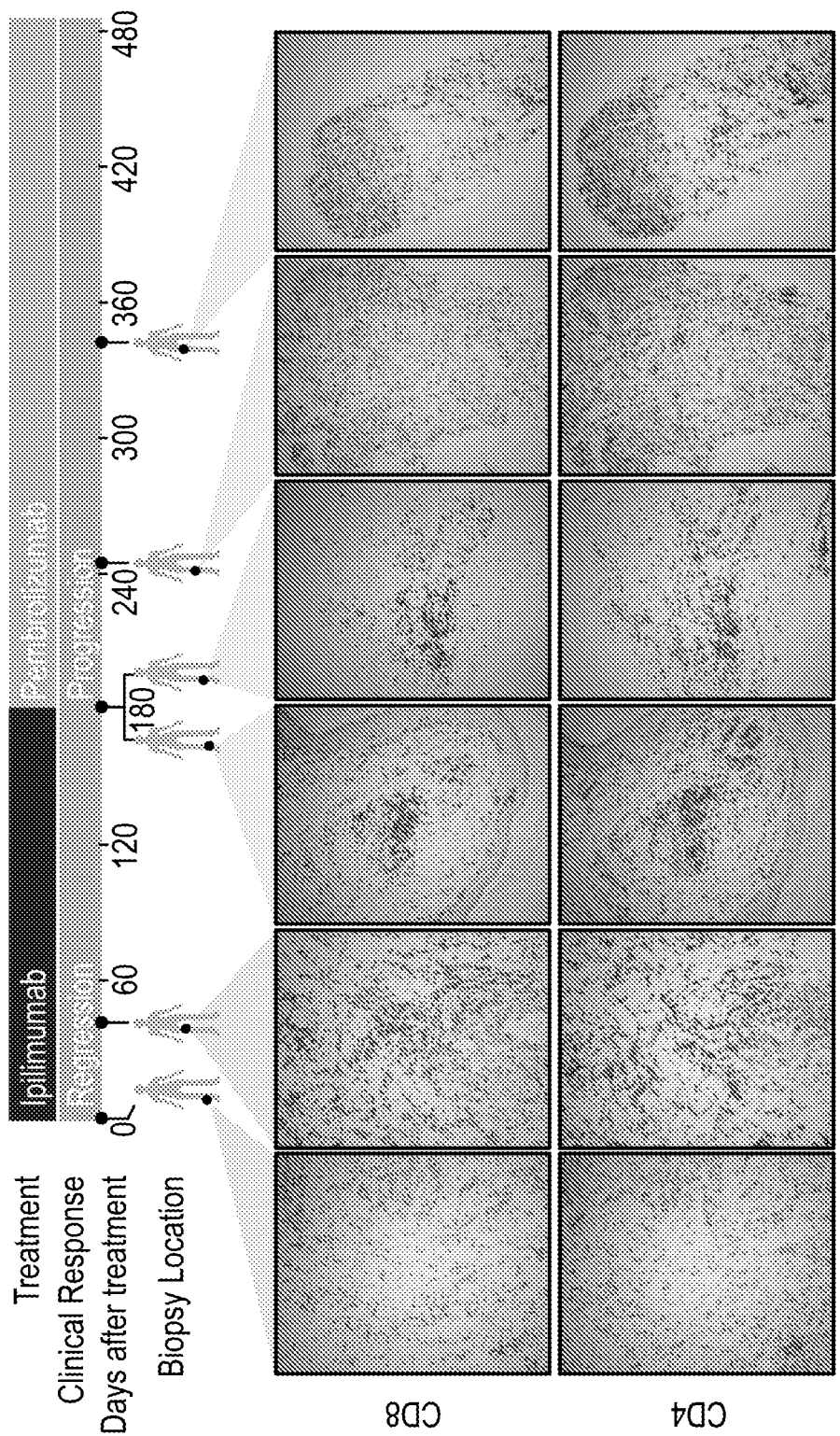
FIG. 5 provides a set of biopsy images. Samples for each time point from Pat208 were stained with specific antibodies against CD8 (top row) or CD4 (bottom row). A timeline of treatment, clinical response, and biopsy locations is shown at the top. Original magnification ×100.
Figure 6:
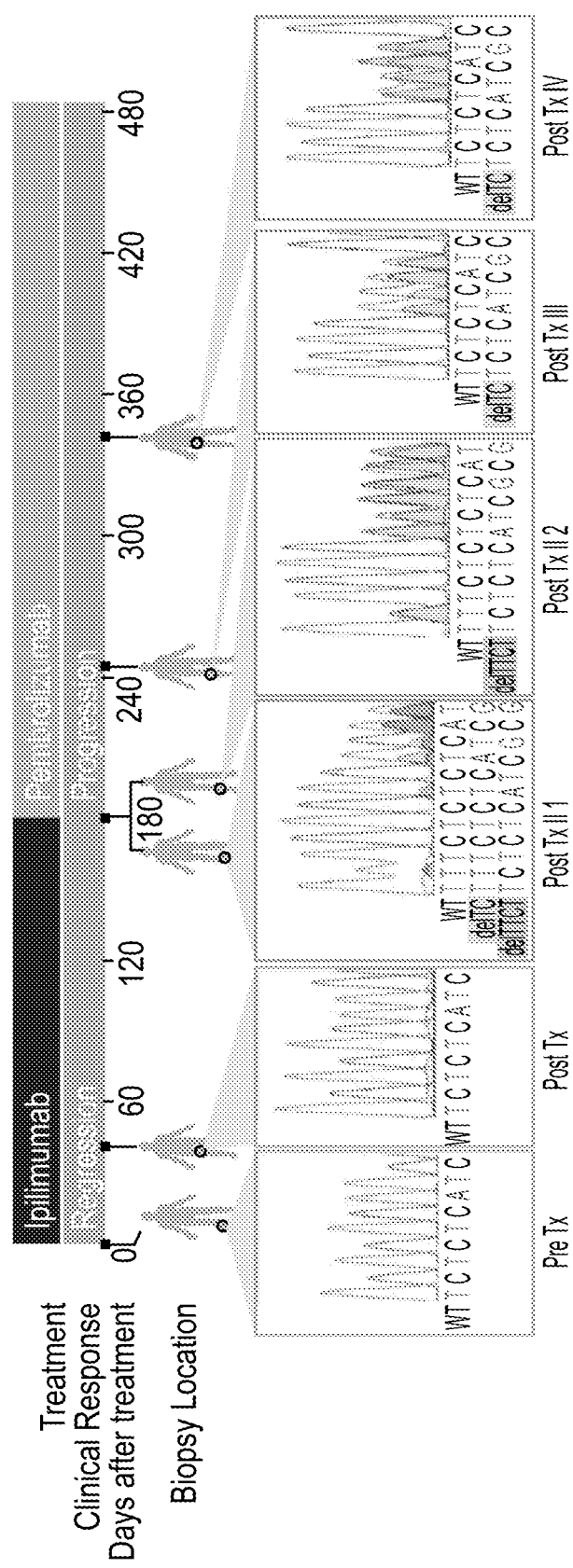
FIG. 6 illustrates the identification of B2M mutations by Sanger sequencing. Sanger sequencing of the region surrounding the identified B2M mutations was performed for six biopsies taken from Pat208. Regression biopsies are outlined in blue, and progression biopsies are outlined in orange. Regions where reads support mutations are colored in light red. Ipilimumab-anti-CTLA4, Pembrolizumab-anti-PD1.

Because checkpoint therapy depends on cytotoxic CD8+ T cell (CTL) recognition of cancer-specific antigens presented on human leukocyte antigen (HLA) class-I complexes[49,9], these therapies could also be affected by changes in the tumor-microenvironment. Checkpoint therapy blocks co-inhibitory ligands expressed on cancer cells and infiltrating myeloid cells (PD-L1) or their receptors on tumor infiltrating T cells (TILs) (PD-1, CTLA4), unleashing anti-cancer T cell immunity[9]. To determine changes in the immune cell infiltrate of tumors from Pat208, RNA sequencing data of bulk tumor was used to infer infiltrating immune cell types and states (such as exhaustion, activation or cytotoxicity for T cells) (FIG. 4). An overall increase in cytotoxicity, co-stimulatory receptors, and the presence of antigen presenting cells (e.g., pDCs, macrophages and B cells) was accompanied by CD8+ and NK cells infiltration during disease regression, but not during progression. In agreement with bulk expression data, IHC staining for CD4+ and CD8+ T cells (FIG. 5) showed a dramatic decrease in CD8+ TILs but not CD4+ cell during progressive disease after B2M loss, as expected by the inability of CD8+ T cells to recognize B2M-deficient tumors.

Several other patients in the cohort exhibited additional B2M alterations. Two B2M frameshift mutations were discovered, p.Ser14fs (50-90% of cancer cells) and p.Gly63fs (70-90% of cancer cells), in post-progression samples of PatT33, who initially responded for one year to ipilimumab. At baseline, p.Gly63fs was detected in 1/429 reads, and p.Ser14fs was undetectable (0/475). However, due to the low tumor purity of this baseline sample, no conclusions can be drawn about these two mutations as drivers of CPB resistance. The presence of multiple frameshift mutations in B2M found in Pat208 and PatT33 suggested that this might be a mutation hotspot. Indeed, TCGA mutation data showed a cluster of B2M mutations at Ser14 (FIG. 10a). All B2M mutations found in this cohort lie within 4× dinucleotide repeats (FIG. 10b), some of which were seen in high-level microsatellite instability colorectal cancers[14], thus implicating faulty DNA mismatch repair (MMR). No DNA mutations in MMR (MLH1, MSH2, MSH3, MSH6, PMS2) were found in Pat208. A somatic mutation in MSH2, p.P476S, was found in Post-Tx and Post-Tx-II samples of PatT33.

Figure 7:
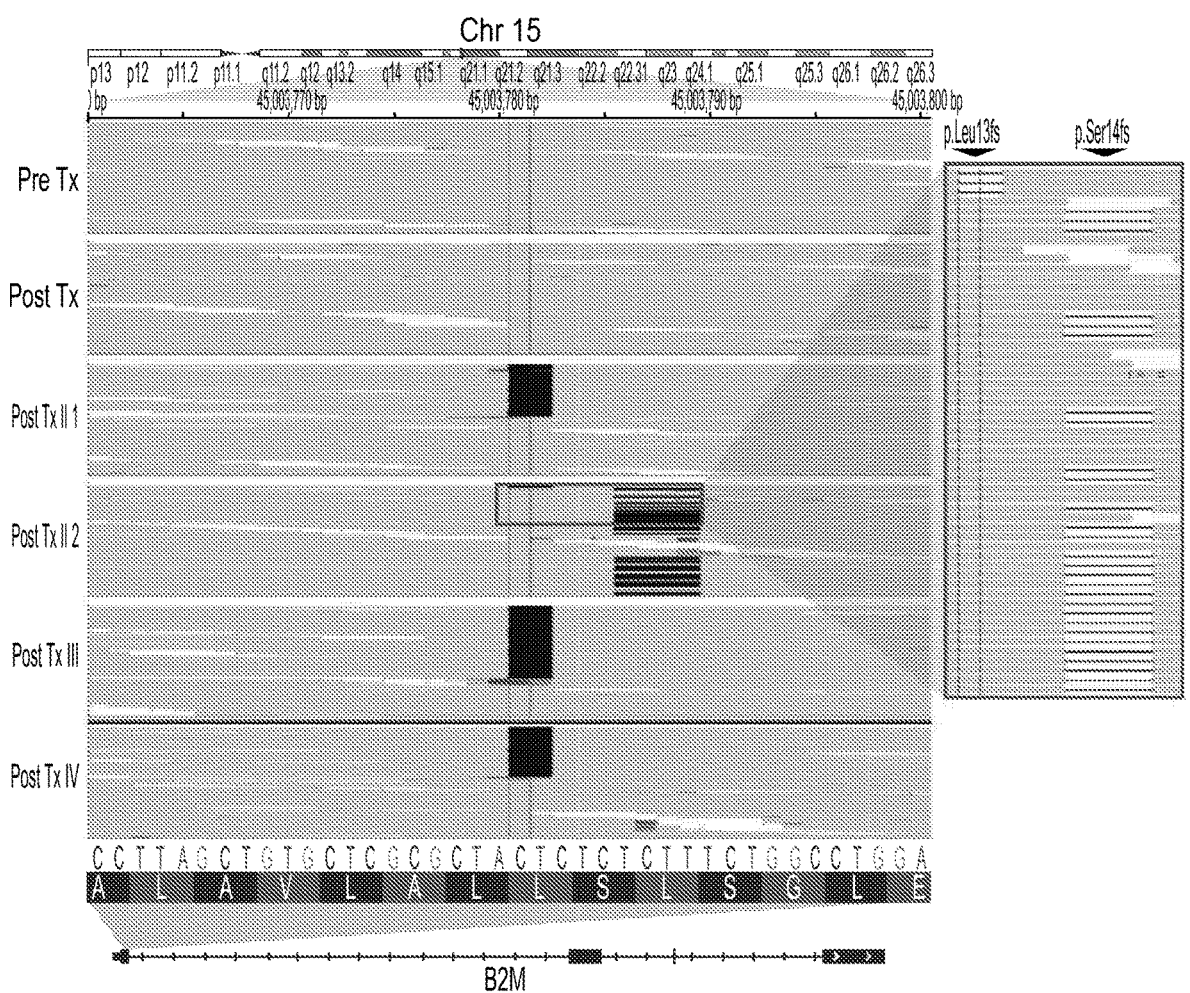
FIG. 7 illustrates an IGV plot of Pat208. BAM files containing sequencing data from Pat208 biopsies were viewed in the Integrated Genome Viewer (IGV). The region of chr15:45,003,761-45,003,800, containing the two frameshift mutations in B2M, is shown. Black bars indicate reads supporting deletions. Reads are sorted by the base in between the black vertical lines at the center of the screenshot, thus all reads supporting deletions are shown at top. Biopsy names are shown on the left. The inset shows an expanded view of reads in Post Tx II 2 biopsy, highlighting the coexistence of the reads in both p.Leu13fs and p.Ser14fs. No reads support both mutations.

To explore whether B2M protein expression is altered post-progression, immunohistochemistry (IHC) was performed on biopsies taken from all patients. Consistent staining of tumor-specific B2M was observed in 2 biopsies from a CPB responder with no B2M aberrations; specificity was validated by showing lack of tumor-specific B2M staining in 2 biopsies from a non-responder harboring a deletion of B2M. As expected from the identified B2M frameshift mutations, a dramatic drop in B2M protein levels occurred after Pat208 developed CPB resistance. Although IHC analysis of the pretreatment sample from Pat33 could not be scored due to low tumor content, Post Tx and Post Tx II both showed no tumor-specific B2M expression, as expected from the two B2M frameshift mutations. B2M expression in Pat99 also fell drastically at the onset of CPB resistance. Although Pat99 had a single B2M deletion at all time points (FIG. 7), loss of B2M expression was only seen post-progression, suggesting that the decrease in B2M expression could be attributed to epigenetic suppression or other genetic causes that suppressed the remaining B2M expression as the tumor evolved. Collectively, these results highlight IHC staining for B2M as a potential diagnostic tool for identifying patients who will not respond to CPB therapy.

In addition to the B2M mutations found in two patients who developed resistance to CPB, B2M LOH was seen in all samples from another progressing patient with initial disease regression of 2.5 months (Pat99) following treatment with nivolumab (anti-PD-1) (FIG. 8a). IHC staining showed loss of tumor-specific B2M protein expression during and after progressive disease, but not while the patient was responding (FIG. 8b). Two more non-responders, Pat25 and Pat115, had B2M LOH (FIG. 11). In contrast to Pat99, loss of tumor-specific B2M protein expression was found in all samples from Pat25 (FIG. 8c). No slides were available for Pat115. Validation of B2M expression in a responder (Pat272) showed no changes in tumor-specific expression over time (FIG. 8d). Collectively, five out of 17 patients in our cohort exhibited B2M alterations, with three of five patients who responded and then progressed, and two of eight non-responders. No B2M alterations were detected in responders (five out of 17 patients) within our cohort.

After identifying B2M mutations post-progression, other genes involved in the antigen processing pathway were evaluated. A LA-C mutation was detected, p.W23C, in Pat208 biopsies taken during disease regression. However, this mutation disappeared in all samples post-progression. In Pat33, TAP2 p.S474F and STAT1 p.R649C were observed in Post Tx and Post Tx II, the first gene being essential in loading antigens to the HLA class I/B2M complex and the second for initiating HLA transcription[10,18]. No LOH was found for either TAP2 or STAT1. Thus, while STAT1 and TAP2 inactivation may provide plausible mechanisms of CPB resistance, the cohort provides stronger evidence for the role of B2M inactivation.

While recent evidence suggested neoantigen load as a predictor of CPB response[19], neoantigen load does not appear to change drastically during CPB. Only subclonal gene count changed substantially in some patients, showing both increases and decreases. The lack of strong trends in neoantigen and mutational load is expected in cells that cannot present neoantigens in the absence of functional B2M, or other factors related to the antigen processing pathway.

Figure 9:
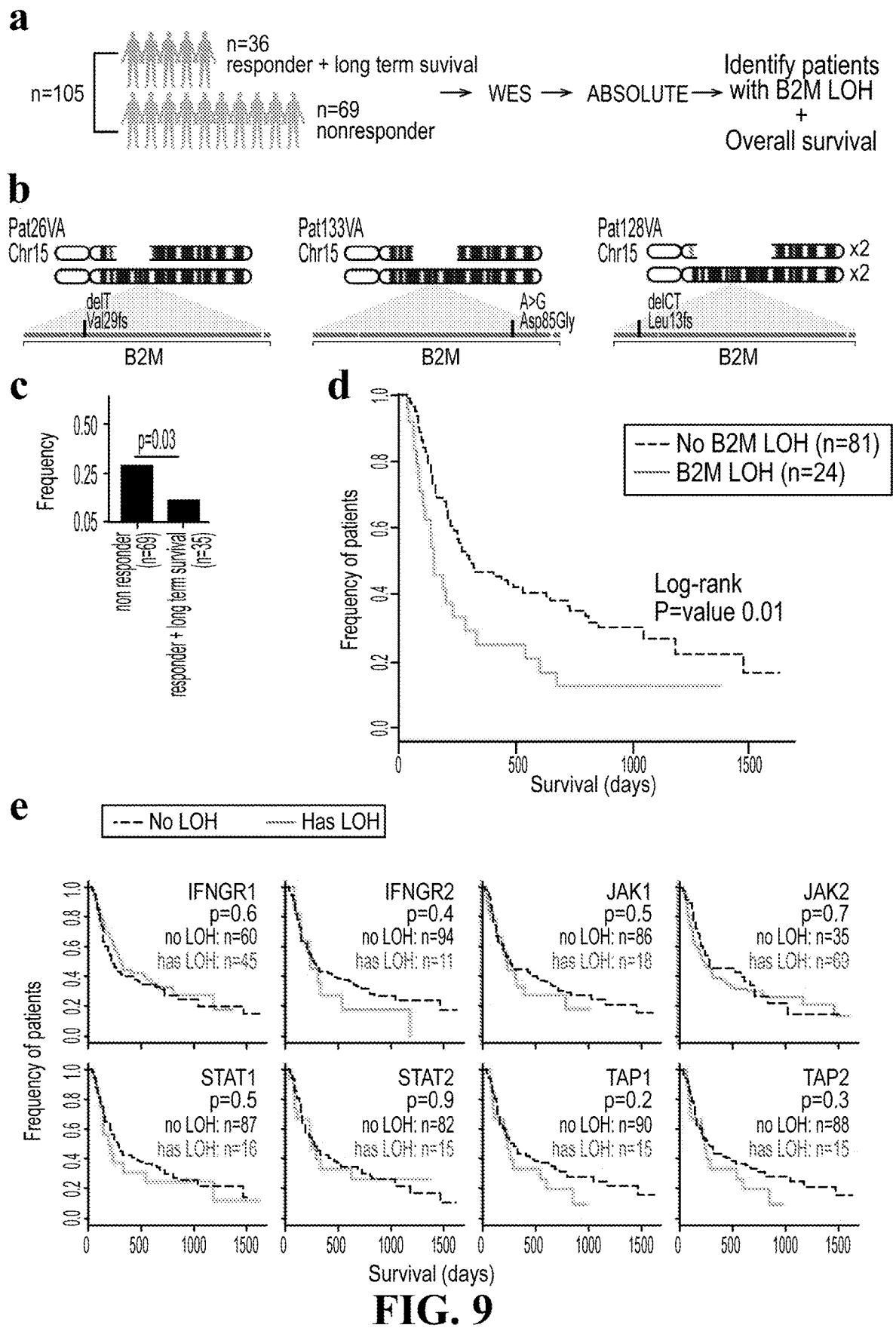
FIG. 9 provide data showing the clinical relevance of B2M mutations in an independent cohort of 105 patients treated with anti-CTLA4. (a) Analysis workflow. Paired tumor and normal biopsies from a total of 36 responders and long-term survivors and 69 non-responders were whole exome sequenced. Analysis of this independent cohort proceeded identically to our cohort. (b) Illustration of three patients in this dataset found to have mutations in B2M accompanied by loss of the wild type allele. Gaps in the top chromosome depict the deleted region in each patient. Exons in B2M are shown as a horizontal blue rectangle, with mutations found in each patient highlighted in red. (c) Frequency of patients with B2M LOH in non-responders versus responders and long-term survivors. One-sided Fisher's exact p-value is shown (P<0.03). (d) Kaplan-Meier survival curves for patients with (red) and without (black) B2M LOH. Log-rank p-value is shown (P<0.01). (e) Kaplan-Meier curves for patients with (red) and without (black) LOH in genes related to the antigen presentation machinery. The numbers of patients with and without LOH are indicated. Note that total cohort size varies based on whether a chromosomal region could be called by our pipeline.

In an independent cohort of 110 patients treated with anti-CTLA4[20], B2M aberrations were found to be significantly enriched in non-responders and significantly associated with survival. After filtering out five biopsies with low tumor content, this dataset was composed of 26 responders, 69 non-responders, and 10 patients who were defined as long-term survivors with no objective clinical response, as defined by RECIST criteria (FIG. 9a). Two frameshift and one missense B2M mutations, including p.Leu13fs, were discovered in three non-responders (FIG. 9b). In all three, B2M LOH also occurred. As our data implicated B2M LOH as a more frequent form of B2M alteration and a potential precursor to the loss of B2M protein expression, the presence of B2M LOH was investigated in this large cohort. B2M LOH events were significantly enriched in non-responders (20/69 vs. 4/36, one-sided Fisher's exact p=0.03) (FIG. 9c), and significantly associated with lower overall survival (log-rank p=0.01) (FIG. 9d). In this large cohort, JAK1 mutations were found in four non-responders and three responders. JAK2 mutations were found in one responder and one long-term survivor, but not in non-responders. B2M mutations, although infrequent, were found only in non-responders. Additionally, unlike B2M, LOH in genes involved in the interferon gamma and antigen presentation pathway were not significantly enriched in non-responders, and did not significantly associate with lower overall survival (FIG. 9e).

Figure 15:
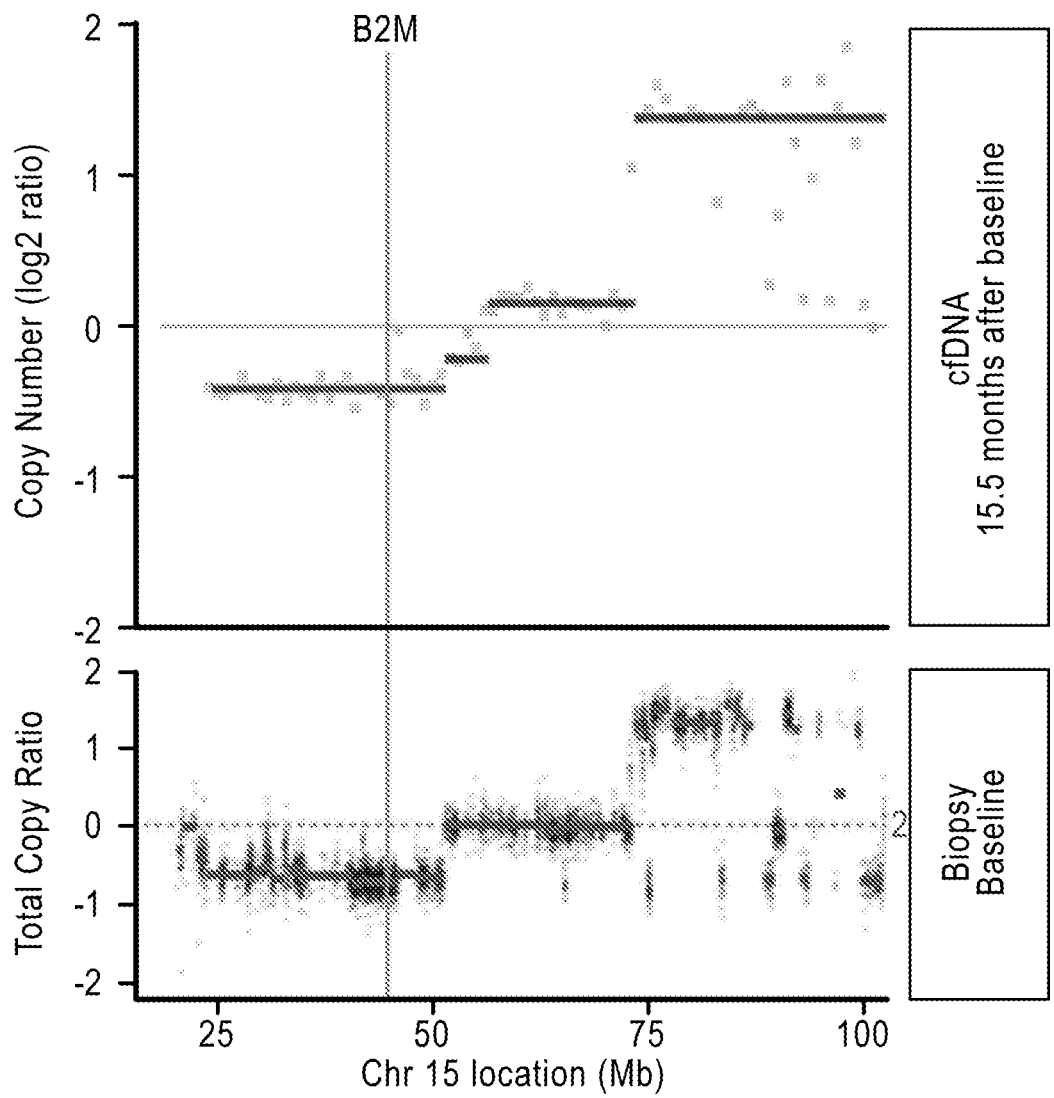
FIG. 15 illustrates the detection of B2M mutation and LOH in cfDNA. (a) cfDNA was isolated from a blood biopsy taken from Pat99 15.5 months after initiation of CPB therapy when the patient was progressing. Results from ReCapSeg of cfDNA (upper panels) and baseline biopsy (lower panel) are shown after performing WES on cfDNA sample. The vertical axis indicates position on chromosome 15. The horizontal axis indicates the total copy number ratio of targets. Each dot indicates a target region used to calculate copy ratio information. Solid red horizontal lines are segments inferred by the ReCapSeg algorithm. Dashed red lines indicate copy ratio corresponding to a total copy number of two, as inferred by ABSOLUTE. (b) cfDNA was isolated from a blood biopsy from Pat208 24.3 months after the baseline sample was taken. Results show the abundances of both NRAS p.Q61R mutation (used as positive control) and B2M p.L13fs, using specific probes and ddPCR.

These studies show that B2M aberrations are significant predictors of response to ipilimumab and overall survival, and that staining for B2M in tumor biopsies can be an effective way of determining whether patients will benefit from CPB. Sequencing of cell-free DNA isolated from blood samples detected B2M frameshifts in Pat208 and B2M LOH could be seen in Pat99 (FIG. 15). Although sequencing cell-free DNA from blood samples may be complicated by low tumor content, it also provides a minimally invasive way of monitoring tumor mutations for patients undergoing CPB. Overall, these results show a fundamental mechanism of clinically acquired CPB resistance or refractory disease through the loss of B2M, and should stimulate development of new diagnostic and therapeutic strategies, such as NK cell induction[41,42], to target B2M/HLA Class I-deficient tumor cells.

INCORPORATION BY REFERENCE

All publications, patents, and patent applications mentioned herein are incorporated by reference to the same extent as if each individual publication, patent or patent application was specifically and individually indicated to be incorporated by reference in its entirety. Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

REFERENCES

1. Robert C, Schachter J, Long G V, et al. Pembrolizumab versus Ipilimumab in Advanced Melanoma. N Engl J Med 2015; 372:2521-32.
2. Weber J S, D'Angelo S P, Minor D, et al. Nivolumab versus chemotherapy in patients with advanced melanoma who progressed after anti-CTLA-4 treatment (CheckMate 037): a randomised, controlled, open-label, phase 3 trial. Lancet Oncol 2015; 16:375-84.
3. Hamid O, Robert C, Daud A, et al. Safety and tumor responses with lambrolizumab (anti-PD-1) in melanoma. N Engl J Med 2013; 369:134-44.
4. Herbst R S, Soria J C, Kowanetz M, et al. Predictive correlates of response to the anti-PD-L1 antibody MPDL3280A in cancer patients. Nature 2014; 515:563-7.
5. Hodi F S, O'Day S J, McDermott D F, et al. Improved survival with ipilimumab in patients with metastatic melanoma. N Engl J Med 2010; 363:711-23.

6. Zou W, Wolchok J D, Chen L. PD-L1 (B7-H1) and PD-1 pathway blockade for cancer therapy: Mechanisms, response biomarkers, and combinations. Sci Transl Med 2016; 8:328rv4.
7. Blank C U, Haanen J B, Ribas A, Schumacher T N. CANCER IMMUNOLOGY. The "cancer immunogram". Science 2016; 352:658-60.
8. Topalian S L, Taube J M, Anders R A, Pardoll D M. Mechanism-driven biomarkers to guide immune checkpoint blockade in cancer therapy. Nat Rev Cancer 2016; 16:275-87.
9. Pardoll D M. The blockade of immune checkpoints in cancer immunotherapy. Nat Rev Cancer 2012; 12:252-64.
10. Hulpke S, Tampe R. The MHC I loading complex: a multitasking machinery in adaptive immunity. Trends Biochem Sci 2013; 38:412-20.
11. Hodis E, Watson I R, Kryukov G V, et al. A landscape of driver mutations in melanoma. Cell 2012; 150:251-63.
12. Berger M F, Hodis E, Heffernan T P, et al. Melanoma genome sequencing reveals frequent PREX2 mutations. Nature 2012; 485:502-6.
13. Rooney M S, Shukla S A, Wu C J, Getz G, Hacohen N. Molecular and genetic properties of tumors associated with local immune cytolytic activity. Cell 2015; 160:48-61.
14. Kloor M, Michel S, Buckowitz B, et al. Beta2-microglobulin mutations in microsatellite unstable colorectal tumors. Int J Cancer 2007; 121:454-8.
15. del Campo A B, Kyte J A, Carretero J, et al. Immune escape of cancer cells with beta2-microglobulin loss over the course of metastatic melanoma. Int J Cancer 2014; 134:102-13.
16. Challa-Malladi M, Lieu Y K, Califano O, et al. Combined genetic inactivation of beta2-Microglobulin and CD58 reveals frequent escape from immune recognition in diffuse large B cell lymphoma. Cancer Cell 2011; 20:728-40.
17. Restifo N P, Marincola F M, Kawakami Y, Taubenberger J, Yannelli J R, Rosenberg S A. Loss of functional beta 2-microglobulin in metastatic melanomas from five patients receiving immunotherapy. J Natl Cancer Inst 1996; 88:100-8.
18. Christova R, Jones T, Wu P J, et al. P-STAT1 mediates higher-order chromatin remodelling of the human MHC in response to IFNgamma. J Cell Sci 2007; 120:3262-70.
19. Riaz N, Morris L, Havel J J, Makarov V, Desrichard A, Chan T A. The role of neoantigens in response to the immune checkpoint blockade. Int Immunol 2016.
20. Van Allen E M, Miao D, Schilling B, et al. Genomic correlates of response to CTLA-4 blockade in metastatic melanoma. Science 2015; 350:207-11.
21. Igney F H, Krammer P H. Immune escape of tumors: apoptosis resistance and tumor counterattack. J Leukoc Biol 2002; 71:907-20.
22. Krasnova Y, Putz E M, Smyth M J, Souza-Fonseca-Guimaraes F. Bench to bedside: N K cells and control of metastasis. Clin Immunol 2015.
23. Langers I, Renoux V M, Thiry M, Delvenne P, Jacobs N. Natural killer cells: role in local tumor growth and metastasis. Biologics 2012; 6:73-82.
24. Pfirschke C, Engblom C, Rickelt S, et al. Immunogenic Chemotherapy Sensitizes Tumors to Checkpoint Blockade Therapy. Immunity 2016; 44:343-54.
25. Wagle N, Grabiner B C, Van Allen E M, et al. Response and acquired resistance to everolimus in anaplastic thyroid cancer. N Engl J Med 2014; 371:1426-33.
26. Van Allen E M, Miao D, Schilling B, et al. Genomic correlates of response to CTLA-4 blockade in metastatic melanoma. Science 2015; 350:207-11.
27. Fisher S, Barry A, Abreu J, et al. A scalable, fully automated process for construction of sequence-ready human exome targeted capture libraries. Genome Biol 2011; 12:R1.
28. Chapman M A, Lawrence M S, Keats J J, et al. Initial genome sequencing and analysis of multiple myeloma. Nature 2011; 471:467-72.
29. Lohr J G, Stojanov P, Lawrence M S, et al. Discovery and prioritization of somatic mutations in diffuse large B-cell lymphoma (DLBCL) by whole-exome sequencing. Proc Natl Acad Sci USA 2012; 109:3879-84.
30. Cibulskis K, Lawrence M S, Carter S L, et al. Sensitive detection of somatic point mutations in impure and heterogeneous cancer samples. Nat Biotechnol 2013; 31:213-9.
31. Ramos A H, Lichtenstein L, Gupta M, et al. Oncotator: cancer variant annotation tool. Hum Mutat 2015; 36:E2423-9.
32. Carter S L, Cibulskis K, Helman E, et al. Absolute quantification of somatic DNA alterations in human cancer. Nat Biotechnol 2012; 30:413-21.
33. Deshwar A G, Vembu S, Yung C K, Jang G H, Stein L, Morris Q. PhyloWGS: reconstructing subclonal composition and evolution from whole-genome sequencing of tumors. Genome Biol 2015; 16:35.
34. Shukla S A, Rooney M S, Rajasagi M, et al. Comprehensive analysis of cancer-associated somatic mutations in class I HLA genes. Nat Biotechnol 2015; 33:1152-8.
35. Hoof I, Peters B, Sidney J, et al. NetMHCpan, a method for MEW class I binding prediction beyond humans. Immunogenetics 2009; 61:1-13.
36. Cerami E, Gao J, Dogrusoz U, et al. The cBio cancer genomics portal: an open platform for exploring multidimensional cancer genomics data. Cancer Discov 2012; 2:401-4.
37. Gao J, Aksoy B A, Dogrusoz U, et al. Integrative analysis of complex cancer genomics and clinical profiles using the cBioPortal. Sci Signal 2013; 6:pl1.
38. Robinson J T, Thorvaldsdottir H, Winckler W, et al. Integrative genomics viewer. Nat Biotechnol 2011; 29:24-6.
39. Zaretsky, J M et al. Genomic correlates of response to CTLA-4 blockade in metastatic melanoma. Science 350, 819-829 (2016).
40. Tumeh, P. C., et al. PD-1 blockade induces responses by inhibiting adaptive immune resistance. Nature 515, 568-571 (2014).
41. Gasser, S. et al. The DNA damage pathway regulates innate immune system ligands of the NKG2D receptor. Nature 436, 1186-1190 (2005).
42. Raulet, D. H. et al. Regulation of ligands for the NKG2D activator receptor. Annu Rev Immunol 31, 413-441 (2013).

What is claimed is:

1. A method for treating cancer in a patient resistant to CPB therapy, said method comprising:
   detecting, in a tumor sample from the patient, one or more genetic modifications in the B2M gene, wherein the one or more genetic modifications are selected from the group consisting of: the combination of a p.Leu13fs and p.Ser14fs frame-shift mutation, the combination of a p.Gly63fs and p.Ser14fs frame-shift mutation, a p.Leu13fs frame-shift mutation, and a p.Gly63fs frame-shift mutation;
   treating the patient with a CPB therapy if the one or more genetic modifications are not detected, or treating the patient with a therapy other than CPB therapy if the one or more genetic modifications are detected.

2. The method of claim 1, further comprising detecting a mutation or deletion in chromosome 15, wherein the mutation or deletion results in loss of heterozygosity (LOH) of the beta-2-microglobulin (B2M) gene.

3. The method of claim 1, wherein said sample is a blood sample or tumor biopsy sample.

4. The method of claim 1, wherein the cancer is a melanoma.

5. The method of claim 1, wherein the genetic modification is detected by sequencing, optionally, wherein sequencing comprises whole exome sequencing.

6. The method of claim 1, wherein the patient has not received CPB therapy; or
   wherein the patient is receiving CPB therapy; or
   wherein the patient has relapsed after receiving CPB therapy.

7. The method of claim 1, wherein said CPB therapy comprises treatment with anti-CTLA4, anti-PD1, anti-PDL1 antibodies or a combination thereof.

8. The method of claim 1, wherein the therapy other than CPB therapy is selected from the group consisting of NK cell therapy, radiotherapy, chemotherapy, and tumor-specific monoclonal antibodies, optionally, wherein said NK cell therapy is an adoptive NK cell therapy and/or treatment with an agonistic antibody directed against an NK cell receptor, or wherein the agonistic antibody is selected from anti-CD137, anti-CD27, and anti-OX40.

9. The method of claim 1, further comprising restoring the genetic modification in the B2M gene using gene therapy.

10. A method for treating cancer in a patient resistant to CPB therapy, said method comprising:
    staining a tumor sample from the patient for B2M protein and one or more markers specific to tumor cells;
    determining the expression of B2M protein based on B2M staining in tumor cells stained by the one or more markers specific to tumor cells, wherein the B2M expression is scored based on the percentage of B2M expressing cells in the tumor fraction, such that Minimal is 0-10%; Low is 10-50%; Intermediate is 50-80%; and High is 80-100%; and treating the patient with a CPB therapy if B2M expression is Low, Intermediate, or High, or treating the patient with a therapy other than CPB therapy if B2M is Minimal.

11. The method of claim 10, wherein the cancer is a melanoma; or
wherein the patient has not received CPB therapy; or
wherein the patient is receiving CPB therapy; or
wherein the patient has relapsed after receiving CPB therapy; or
wherein said CPB therapy comprises treatment with anti-CTLA4, anti-PD1, anti-PDL1 antibodies or a combination thereof; or
wherein the therapy other than CPB therapy is selected from the group consisting of NK cell therapy, radiotherapy, chemotherapy, and tumor-specific monoclonal antibodies, optionally, wherein said NK cell therapy is an adoptive NK cell therapy and/or treatment with an agonistic antibody directed against an NK cell receptor, or wherein the agonistic antibody is selected from anti-CD137, anti-CD27, and anti-OX40; or
wherein said sample is a tumor biopsy sample.

12. The method of claim 1, wherein the one or more genetic modifications are detected in cell-free DNA isolated from a blood sample from the patient.

* * * * *

UNITED STATES PATENT AND TRADEMARK OFFICE
CERTIFICATE OF CORRECTION

| | |
|---|---|
| PATENT NO. | : 11,634,777 B2 |
| APPLICATION NO. | : 16/477827 |
| DATED | : April 25, 2023 |
| INVENTOR(S) | : Nir Hacohen et al. |

It is certified that error appears in the above-identified patent and that said Letters Patent is hereby corrected as shown below:

In the Specification

In Column 10, Line 26, delete "β" and insert -- β2 --.

In Column 12, Line 5, delete "4(54" and insert -- Δ(54 --.

In Column 12, Line 6, delete "4(91" and insert -- Δ(91 --.

In Column 12, Line 6, delete "4(103" and insert -- Δ(103 --.

In Column 12, Line 6, delete "4(97" and insert -- Δ(97 --.

In Column 12, Line 6, delete "4(239" and insert -- Δ(239 --.

In Column 19, Line 19, delete "Deparafinization" and insert -- Deparaffinization --.

In Column 19, Line 20, delete "retreival" and insert -- retrieval --.

In Column 19, Line 27 (approx.), delete "tempature" and insert -- temperature --.

In Column 22, Lines 6-7, delete "complexes$^{49,9}$," and insert -- complexes$^{40,9}$ --.

Signed and Sealed this
Nineteenth Day of December, 2023

Katherine Kelly Vidal
*Director of the United States Patent and Trademark Office*